United States Patent
Chambers

(10) Patent No.: US 10,889,790 B2
(45) Date of Patent: Jan. 12, 2021

(54) GROWTH OF BACTERIAL HOST CELLS IN GAS PERMEABLE LOW-DENSITY POLYETHYLENE BAGS FOR PRODUCTION OF PLASMID DNA OR RECOMBINANT MOLECULES

(71) Applicant: ALDEVRON, LLC, Fargo, ND (US)

(72) Inventor: Isabelle Louise Chambers, Fargo, ND (US)

(73) Assignee: ALDEVRON, LLC, Fargo, ND (US)

( * ) Notice: Subject to any disclaimer, the term of this patent is extended or adjusted under 35 U.S.C. 154(b) by 0 days.

(21) Appl. No.: 16/816,187

(22) Filed: Mar. 11, 2020

(65) Prior Publication Data

US 2020/0291338 A1  Sep. 17, 2020

Related U.S. Application Data

(60) Provisional application No. 62/816,664, filed on Mar. 11, 2019.

(51) Int. Cl.
| | |
|---|---|
| *C12N 1/20* | (2006.01) |
| *C12N 1/22* | (2006.01) |
| *C12N 15/70* | (2006.01) |
| *C12N 15/74* | (2006.01) |
| *C12M 1/00* | (2006.01) |
| *C12M 1/04* | (2006.01) |
| *C12P 21/00* | (2006.01) |
| *G01N 1/28* | (2006.01) |

(52) U.S. Cl.
CPC .......... *C12M 23/14* (2013.01); *C12M 23/24* (2013.01); *C12N 15/70* (2013.01); *C12P 21/00* (2013.01); *G01N 1/28* (2013.01)

(58) Field of Classification Search
CPC .......... C12N 5/02; G01N 33/53; C12M 3/00
See application file for complete search history.

(56) References Cited

U.S. PATENT DOCUMENTS

| | | | | |
|---|---|---|---|---|
| 2005/0233390 A1* | 10/2005 | Allen | ............... | G01N 33/54386 435/7.9 |
| 2007/0292945 A1* | 12/2007 | Lin | ........................ | C12M 23/14 435/325 |
| 2012/0258502 A1* | 10/2012 | Pandiripally | ...... | C12N 15/1003 435/91.4 |

OTHER PUBLICATIONS

Bakker, et al., "Small-scale GMP production of plasmid DNA using a simplified and fully disposable production method," Journal of Biotechnology: X, 2019, pp. 1-8.

Glazyrina, et al., High cell density cultivation and recombinant protein production with *Escherichia coli* in a rocking-motion-type bioreactor, BioMed Central, 2010, pp. 1-11.

Junne, et al., "Cultivation of Cells and Microorganisms in Wave-Mixed Disposable Bag Bioreactors at Different Scales," Chemie Ingenieur Tecknik, 2013, pp. 57-66, V.85, No. 1-2.

Mahajan, et al., "Use of Disposable Reactors to Generate Inoculum Cultures for *E. coli* Production Fermentations," American Institute of Chemical Engineers, 2010, pp. 1200-1204.

* cited by examiner

*Primary Examiner* — Maryam Monshipouri
(74) *Attorney, Agent, or Firm* — Maynard Cooper & Gale, P.C.; Matthew J. Parker, Esq.

(57) ABSTRACT

The present disclosure pertains to methods of growing bacterial host cells in a low-density polyethylene (LDPE) bag to produce plasmid DNA or express recombinant protein. The LDPE bag is filled with media, an antibiotic, and host bacterial cells that have been transformed with plasmid DNA encoding a protein of interest. The LDPE bag is sealable to the external environment and incubated at a growth temperature until a desired concentration of bacteria is achieved. When plasmid DNA is desired, host cells are harvested and plasmid DNA is separated from host cell components. When recombinant protein is desired, expression is induced while host cells are in the LDPE bag, followed by the harvest and separation of the recombinant protein. The LDPE bags are sterile and conducive to bacterial growth equal to or greater than that afforded by conventional shake flasks under similar growth conditions.

20 Claims, 41 Drawing Sheets

GROWTH OF BACTERIAL HOST CELLS IN GAS PERMEABLE LOW-DENSITY POLYETHYLENE BAGS FOR PRODUCTION OF PLASMID DNA OR RECOMBINANT MOLECULES

RELATED APPLICATIONS

This application claims priority to U.S. Provisional Patent Application No. 62/816,664 filed on Mar. 11, 2019, titled "Growth of Bacterial Host Cells in Gas Permeable Low-Density Polyethylene Bags for Production of Plasmid DNA or Recombinant Molecules", the entire content of which is incorporated herein.

TECHNICAL FIELD

The present invention is directed to the growth of bacteria in gas-permeable low-density polyethylene bags for the production of plasmid DNA and expression of proteins encoded by genes in the plasmid DNA.

BACKGROUND OF INVENTION

Plasmid DNA and recombinant molecule production at clinical-grade quality are needed for applications such as personalized gene therapy and immunotherapy. For example, ex vivo genetic treatments often require a unique set of plasmids that express genes of interest that are of use for an individual patient. Recombinant proteins are used in drug discovery applications as drugs for specific biological targets, as well as in biomedical research applications. However, current methods of producing these plasmids and recombinant molecules are susceptible to cross-contamination and environmental contamination, and are often expensive.

Plasmid production for personalized ex vivo gene therapy and immunotherapy typically requires small to medium scale plasmid production, and is currently undertaken primarily using bacteria host cell growth in classic shake flasks. These flasks may be used to produce plasmids from bacteria, such as *E. coli* and utilize volumes ranging from 250 mL to 10 L. Typical shake flasks may be glass or plastic, with glass flasks being multi-use and plastic flasks intended for single-use applications. Thus, thorough cleaning of glass flasks is required to ensure sterility, while the replacement of single-use plastic flasks is often not economical. The large-bottomed shape of shake flasks requires expansive space in laboratory incubation equipment, which may reduce the efficiency of the plasmid production process. Further, openings at the top of those flasks used for respiration can result in unintended cross-contamination from other flasks or from the external environment.

An alternative to shake flasks is "cell culture bags", which are commercially available. However, these culture bags are intended for mammalian cell culture and can cost more than $50 per individual bag. That cost is often too high for the practical production of plasmids by bacterial cell culture and the materials that those culture bags are manufactured from are sufficiently thick such that respiration of the cultured cells is not promoted. The present methods for recombinant molecule and plasmid production by bacterial cells instead use gas-permeable low-density polyethylene (LDPE) bags, which are both sealable to the external environment and permit respiration of the cultured cells. LDPE bags are inexpensive, sufficiently sterile for bacterial cell culture, and require minimal space within incubation equipment. The growth of bacterial cells from the disclosed methods results in equal or greater bacterial growth relative to traditional shake flask methods.

SUMMARY OF THE INVENTION

The present invention is directed to methods of growing bacterial host cells in a low-density polyethylene (LDPE) bag to produce plasmid DNA or express recombinant protein. In one aspect of the invention, there is provided a method of growing bacterial host cells in a gas-permeable bag. The method includes the step of providing a starter culture of bacterial host cells, where the starter culture includes at least one colony of the host cells transformed with plasmids having an antibiotic resistance gene. A gas-permeable bag is filled with a volume of media, an antibiotic, and a volume of the starter culture host cells to form a main culture, where the antibiotic is selected so that starter culture host cells expressing the antibiotic resistance gene are viable in the presence of the antibiotic. The gas-permeable bag containing the main culture is incubated so that bacterial host cells grow to a desired concentration.

In some instances, the host cells are *E. coli* cells and the gas-permeable bag is an LDPE bag. The LDPE bag may be sealable using locking panels, so that the LDPE bag is closed to an external environment when sealed. In some embodiments, the plasmids further comprise a DNA sequence encoding a protein to be expressed. The volume of media added to the gas-permeable bag is about 50 mL to 1 L and the incubating of the gas-permeable bag containing the main culture includes agitation at about 200 to 500 rpm in a shaker incubator at a temperature of about 30° C. to 42° C. In some instances, the desired concentration of bacterial host cells is indicated by an $OD_{600}$ of 0.1 to 2.

In another aspect of the invention, there is provided a method of producing plasmid DNA from bacterial host cells grown in a gas-permeable LDPE bag. The method includes filling the LDPE bag with a volume of media, an antibiotic, and a volume of host cells to form a main culture, where at least a portion of the host cells are transformed with plasmids having a DNA sequence encoding a protein and an antibiotic resistance gene, and where the antibiotic is selected so that host cells expressing the antibiotic resistance gene are viable in the presence of the antibiotic. The LDPE bag containing the main culture is incubated and an $OD_{600}$ of the main culture is measured. Host cells are harvested from the main culture when a host cell concentration, indicated by the $OD_{600}$, reaches a desired concentration. The host cells are then pelleted using centrifugation and lysed to obtain a lysate comprising plasmid DNA produced by the host cells.

In some instances, the LDPE bag is sealable using locking top panels, so that the LDPE bag is closed to an external environment when sealed. The volume of media added to the LDPE bag is about 50 mL to 1 L and the incubating of the LDPE bag containing the main culture includes agitation at 200 to 500 rpm in a shaker incubator at a temperature of about 30° C. to 42° C. In some embodiments, the desired concentration of bacterial host cells is indicated by an $OD_{600}$ of about 0.1 to 2. In some embodiments, the method further includes separating cellular components of the host cells from the plasmid DNA within the host cell lysate.

In yet another aspect of the invention, there is provided a method of expressing a target protein in bacterial host cells grown in an LDPE bag. The method includes filling the LDPE bag with about 50 mL to 1 L of media, an antibiotic, and host cells to form a main culture, where at least a portion of the host cells are transformed with plasmids having a DNA sequence encoding the target protein and an antibiotic resistance gene, and where the antibiotic is selected so that host cells expressing the antibiotic resistance gene are viable in the presence of the antibiotic. The LDPE bag containing the main culture is incubated at a growth temperature until the host cell concentration reaches a desired concentration indicated by an $OD_{600}$ of about 0.1 to 2. Expression of the target protein by the host cells of the main culture is then induced.

In some instances, the incubating of the LDPE bag containing the main culture includes agitation at about 200 to 500 rpm in a shaker incubator and at a growth temperature between about 30° C. to 42° C. In some embodiments the induction includes the addition of an inducing agent to the main culture. In other embodiments the induction includes reducing the growth temperature to an induction temperature of about 15° C. to 37° C. In yet other embodiments the induction includes both the addition of an inducing agent and the reduction of the growth temperature to an induction temperature of about 15° C. to 37° C. In some embodiments, the method further includes harvesting host cells from the main culture, pelleting the host cells using centrifugation, lysing a pellet of the host cells to obtain a lysate, and purifying the target protein expressed by the host cells.

A further understanding of the nature and advantages of the present invention will be realized by reference to the remaining portions of the specification and the drawings.

BRIEF DESCRIPTION OF DRAWINGS

The present disclosure can be better understood, by way of example only, with reference to the following drawings. The elements of the drawings are not necessarily to scale relative to each other, emphasis instead being placed upon clearly illustrating the principles of the disclosure. Reference numerals designate corresponding parts throughout the several views.

DETAILED DESCRIPTION OF THE INVENTION

Figure 1:
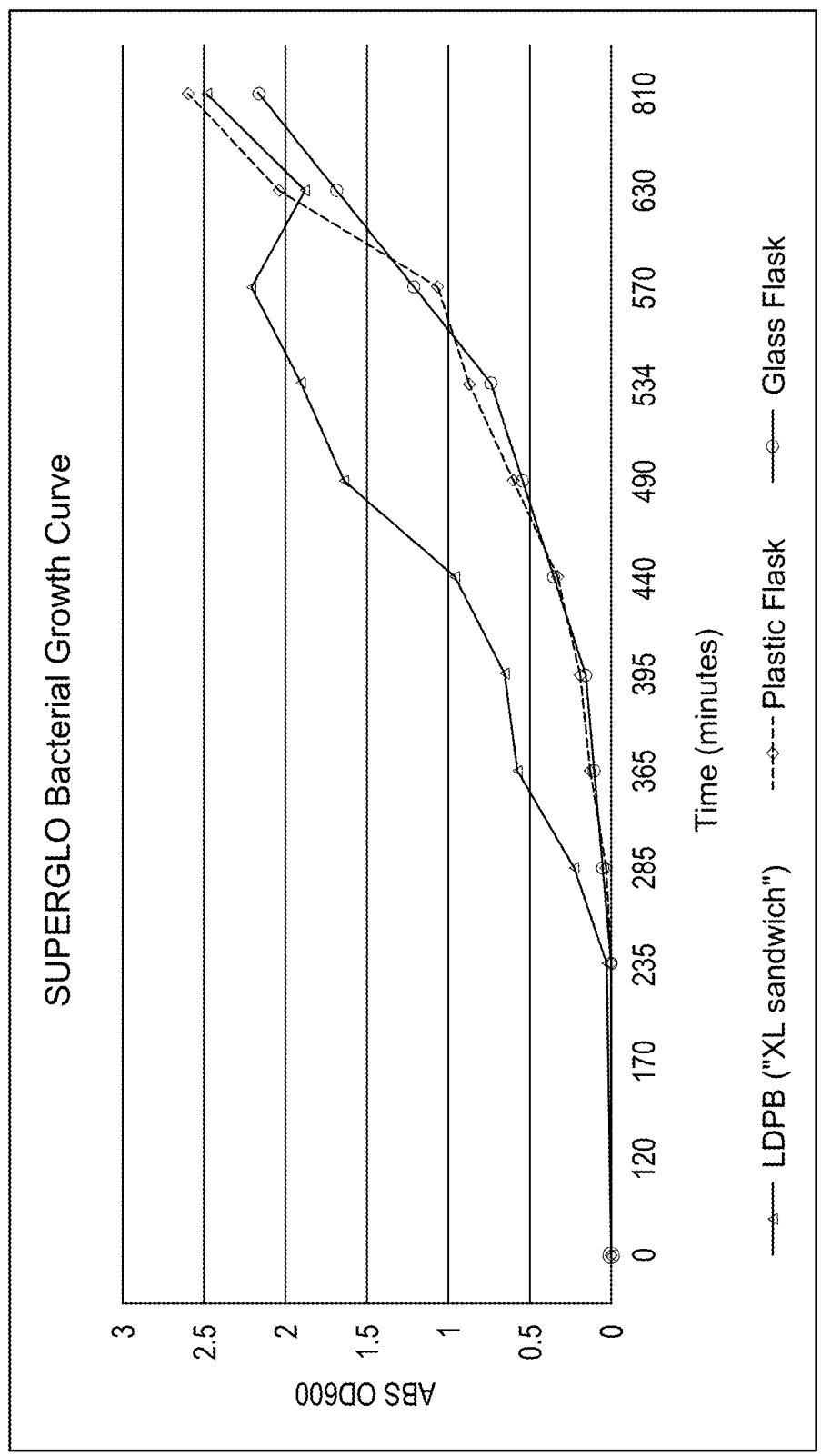
FIG. 1 is a graph illustrating a bacterial growth curve for bacteria grown in a low-density polyethylene (LDPE) bag in accordance with the disclosed method and compared to bacterial growth in a plastic flask and a glass flask.

The present invention is generally directed to methods for growing bacteria in gas-permeable, low-density polyethylene (LDPE) bags 10 for the production of plasmid DNA 18 or recombinant molecules. These methods provide advantages to conventional shake flask methods in that LDPE bags 10 are sealable to prevent contamination from the external environment, are low cost, and require smaller amounts of laboratory incubator equipment space than shake flasks. The present methods provide the same or higher yields of plasmid DNA 18 than conventional methodologies.

Host cells 12 for the present invention include bacteria, such as *Escherichia coli, Corynebacterium, Bacillus subtilis*, and *Pseudomonas fluorescens*. Other bacterial systems not specifically mentioned are compatible with the present methods. The bacterial cells are used as expression hosts for foreign DNA that is introduced into the bacteria. In preferred embodiments, the host bacteria is competent *E. coli*, such as commercially available BL21 competent *E. coli*, DH5a competent *E. coli* families, DH10B competent *E. coli* families, and Stbl competent *E. coli* families, though other competent *E. coli* are compatible with the present methods. The source of foreign DNA includes, but is not limited to, viruses, plasmids, artificial chromosomes or bacteriophage. Generally, the DNA source and host are chosen such that they are compatible, result in optimal DNA production or recombinant molecule expression and protein 20 production, and accommodate the gene to be expressed.

In *E. coli* expression systems, competent *E. coli* host cells are transformed with the gene of interest, often included in a plasmid expression vector. In addition to the gene of interest, expression vectors include additional elements, such as a promoter region, regulator and ribosome binding sites, a transcription terminator, a multiple cloning site, a selection marker, an origin of replication, and other control genes. The gene of interest is ligated at restriction sites and results in the expression of the protein 20 of interest. In many instances, the selection marker is a gene for resistance to a particular antibiotic, which is then used to select transformed bacteria through growth in the presence of that antibiotic. Examples of antibiotics used to select transformed *E. coli* cells include, but are not limited to, ampicillin, kanamycin, and carbenicillin.

Transformation of *E. coli* with plasmid DNA in the present methods precedes the initiation of a starter culture 14. Transformation of competent *E. coli* involves mixing plasmid DNA with the competent *E. coli*, allowing plasmid DNA entry through pores in the bacterial cell membranes. Bacterial host cells 12 utilize their own processes and replication machinery to create copies of the foreign plasmid DNA, including any genes for a protein 20 of interest. In the present method, transformation occurs at temperatures and over time periods recommended by the commercial plasmid provider for the expression system used. For example, for BL21 cells, transformation occurs by first mixing the cells 12 and plasmid on ice, followed by a heat shock and more time on ice, and then adding media and incubating the mixture at 37° C. with agitation. However, different strains of competent *E. coli* and different DNA sources can result in different transformation protocols. Different methods of transformation are compatible with the present methods.

Selection of transformed bacterial host cells 12 is undertaken by plating host cells 12 and selecting for those containing the plasmid. Plates typically include agar and an antibiotic to which the transformed cells are resistant due to their expression of the antibiotic resistance gene. Incubation of plates occurs at approximately 37° C. overnight, or at different incubation times and temperatures based on the desired amount of growth and starting concentrations of bacteria. Colonies of bacterial host cells 12 containing the plasmid DNA grow in the presence of the selection factor. Both positive and negative selection methods are compatible with the disclosed method.

Figure 17:
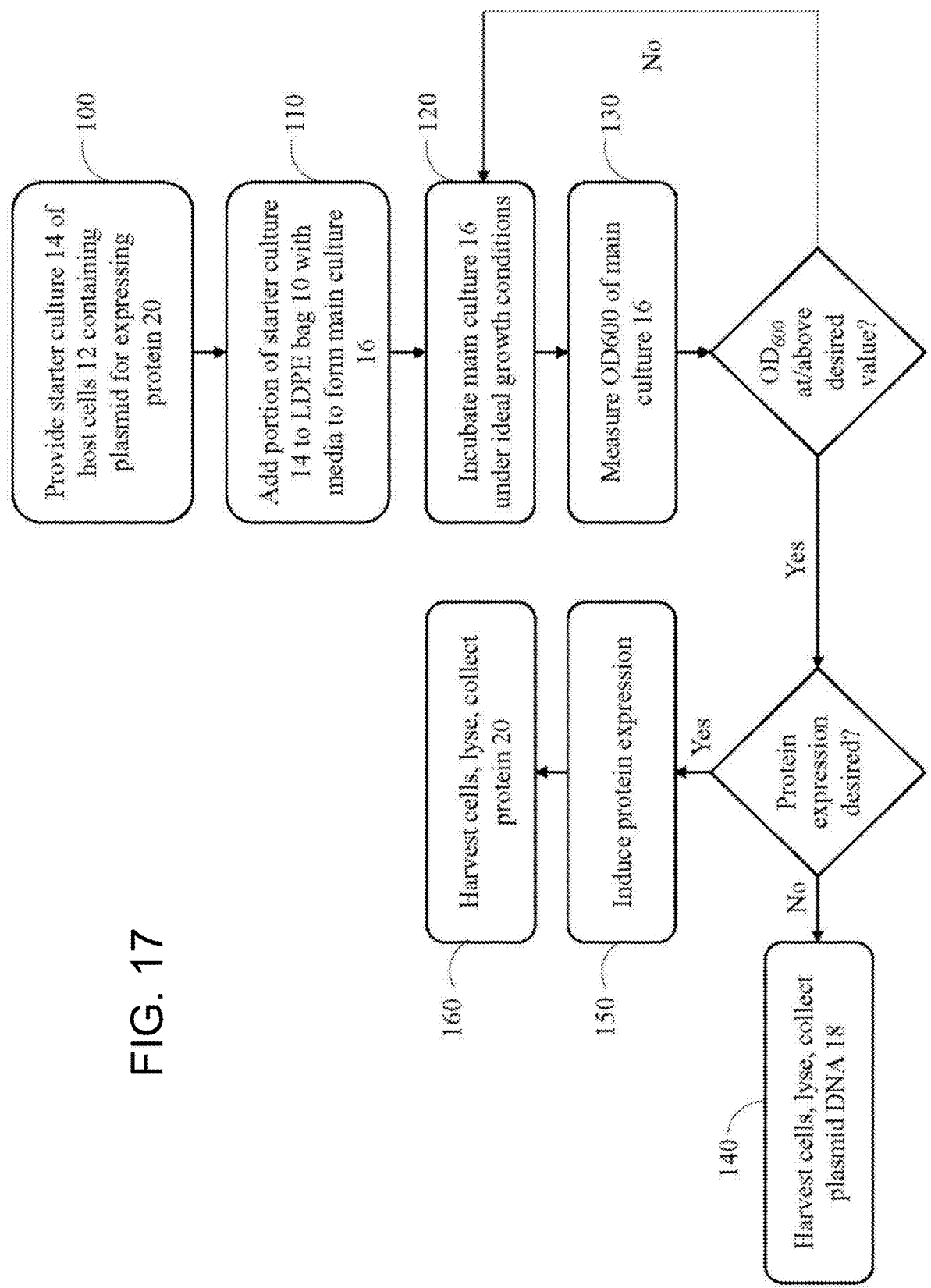
FIG. 17 is a flow chart illustrating the method of bacterial growth in a LDPE bag for plasmid DNA generation or protein expression.

Following the selection of transformed colonies of host cells 12, starter culture 14 is established, as shown in FIG. 17, step 100. The method involves the production of starter culture 14 using approximately 5-50 mL of media, and in some embodiments 10 mL of media in a 50 mL sterile tube. Starter culture 14 further includes the antibiotic used for selection of transformed cells from the plates and at least one colony of host cells 12 from the plate. Cells 12 are added from the plate using aseptic techniques and tools, such an inoculation loop. Starter culture 14 is used to expand the initial colony or colonies to a higher scale and concentration. The choice of culture media varies based on bacterial host cell strain and in some instances is the same media used with agar in the plating step. Common media includes, but is not limited to, Terrific broth (TB), Lysogeny broth (LB), Super Optimal broth (SOB/SOC), and tryptone broth, though other media types are possible. For example, RG media (Rapid Growth Media, Aldevron, Fargo, N. Dak.) and MY media (Maximum Yield Media, Aldevron, Fargo, N. Dak.) are used for starter culture 14 and main culture 16 growth steps. Starter culture 14 is then incubated at a temperature ranging from about 30° C. to 37° C. overnight, or for times appropriate for the desired growth of bacterial host cells 12. Starter culture 14 incubation includes agitation in some instances, and occurs on a shaker incubator or similar agitation equipment at about 100 to 500 rpm, or in some embodiments at about 250 rpm.

After bacterial host cells 12 of starter culture 14 have grown to a desired concentration, a main culture 16 is initiated, as shown in FIG. 17, step 110. Main culture 16 is added to LDPE bags 10 described in the present invention and includes media, an antibiotic, and at least part of starter culture 14. The media is in some cases the same as the media used in starter culture 14, though in other cases it differs. Likewise, the antibiotic is in some instances the same antibiotic used in starter culture 14, though in other cases it differs. In yet other cases, no antibiotic is included in main culture 16. The volume of media used varies with LDPE bag size and the desired amount of host cells 12, plasmids, and/or protein 20. For example, for a small, "sandwich-sized" LDPE bag, 50 mL of media is used, while for a large, "gallon-sized" LDPE storage or freezer bag, up to 1 L of media is used. Other bag sizes include "extra-large sandwich-sized" LDPE bags and medium, "quart-sized" LDPE bags. LDPE bag volumes therefore range from about 50 mL to more than 1 L. For example, 50 mL, 250 mL, or 1 L of media is added to LDPE bag 10, depending on the size of LDPE bag 10. Small LDPE bags measure approximately 6 inches by 9 inches, medium LDPE bags measure approximately 8 inches by 10 inches, and large LDPE bags measure approximately 12 inches by 12 inches in the following examples. However, bag dimensions that are larger or smaller than these examples are compatible with the disclosed method. Bag materials other than low-density polyethylene are possible, such that the material is gas-permeable and capable of being sterilized, which includes, in some instances, methods including UV irradiation or incubation with sterilization solutions, such as a 70% (v/v) ethanol solution. Commercially available LDPE bags 10 used in the following examples were determined to be sterile for the purposes of bacterial cell culture over the growth times used in the disclosed method. For example, Ziploc®-style LDPE bags 10 are compatible with the present methods and were used in the following examples.

The volume of starter culture 14 transferred to main culture 16 depends on the concentration of bacterial host cells 12 present in starter culture 14, the desired growth conditions, and the viability of bacterial host cells 12 in starter culture 14. For example, starter culture 14 volumes of between about 100 µL and 500 µL were used in the following examples, though larger or smaller volumes are possible such that the total volume of main culture 16 does not exceed LDPE bag capacity.

LDPE bags 10 are sealable to contaminants, such as bacteria or phage, from the external environment. The sealing mechanism of the bags includes pressing several panels at a top portion of LDPE bag 10 together to "lock" the panels on each side of the bag together and form a liquid-tight seal. Other sealing methods include a sliding "zipper" that glides along and seals panels on interior, top portions of opposite sizes of LDPE bag 10, clips or band that hold two sides of a bag together, ties or drawstrings that wrap about a top opening of LDPE bag 10, non-reactive adhesives that seal two sides of the bag together at an opening, or other sealing means. The sealing is, preferably, non-permanent and non-destructive to LDPE bag 10, such that LDPE bag 10 is capable of being re-opened without destruction or leaking of its contents. In the present method, LDPE bag 10 is sealed following the addition of main culture components and starter culture cells, and is sealed using a panel-locking mechanism at the top opening of LDPE bag 10.

Following the sealing of main culture 16 within LDPE bag 10, LDPE bag 10 is placed in an incubator for bacterial host cell growth, as described in FIG. 17, step 120. The growth conditions are such that bacterial cell growth is prioritized over protein expression. Thus, growth conditions, such as temperature, agitation rate, $CO_2$ content, humidity, and growth time are varied based on the desired host cell concentration and strain. The following examples illustrate different growth conditions for *E. coli* host cells in different media and with different plasmids. Growth temperatures range from about 30° C. to 42° C. (the growth temperature being a temperature range suitable for growth of cultured cells, with such temperature range varying depending on the cell line and strain used, as well as the desired growth time and protein yield), and agitation rates on a shaker or shaker incubator range from about 50 rpm to over 500 rpm. In general, larger bags and higher temperatures results in more rapid bacterial cell growth. Agitation rates of 300 rpm resulted in more bacterial growth than 200 rpm agitation rates. Growth times are in some instances predetermined, for example, to be about 18 to 24 hours or other empirically determined values. In other instances, growth times vary based on the time it takes for bacterial host cells 12 to reach a desired concentration, indicated by an optical density (OD) value measured at a 600 nm wavelength ($OD_{600}$). For example, the desired $OD_{600}$ value ranges from about 0.05 to more than 2 and varies based on cell line, strain, plasmid DNA 18 production, and desired yield of expressed protein 20. In some instances, $OD_{600}$ values greater or less than this range are desired. The $OD_{600}$ readings are generally taken using a spectrophotometer or similar instrument, shown in FIG. 17, step 130, and are taken at different growth time points to monitor bacterial host cell growth over time.

Upon reaching a desired growth time, $OD_{600}$ value, or other growth indicator or condition, plasmid DNA 18 produced by bacterial host cells 12 is available to be harvested, as shown in FIG. 17, step 140. When recombinant protein production is desired, the induction of protein expression is undertaken at this point. In embodiments where plasmid DNA production is desired, bacterial host cells 12 are harvested from the bags by first unsealing the opening of LDPE bags 10 and transferring the bag contents to one or more sterile containers capable of centrifugation. Cells 12 are pelleted using centrifugation or other gravimetric separation means, such that excessive physical cell damage is minimized. Upon generation of a pellet of bacterial host cells 12, excess supernatant is removed and the pellet is available for lysis steps. Lysis is undertaken using protocols well known in the art, such that bacterial cell components are exposed and plasmid DNA 18 produced by bacterial host cells 12 is released. Plasmid DNA 18 is then purified using methods known in the art and using commercially available kits and reagents, such as anion-exchange kits (Qiagen, Germantown Mass.). Plasmid DNA 18 is separated from cellular components, such as protein, RNA, and cellular, endogenous DNA. The purity of plasmid DNA 18 produced is determined using separation techniques, such as gel electrophoresis. The bands of DNA visible on the electrophoresis gel correspond to the molecular weight of the DNA, and thus illustrate qualitative DNA purity and relative amounts of DNA.

When recombinant protein expression is desired, cells 12 are not harvested until expression of protein 20 is induced, as shown in FIG. 17, step 150. The induction in some instances involves the reduction of temperature from the growth temperature to a lower induction temperature. For instance, the induction temperature ranges from about 20° C. to about 37° C. In some instances, induction involves the addition of an inducing agent to main culture 16. The inducing agent is added in addition to a reduction in temperature in some instances. Inducing agents are selected based on the cell line and strain used, and thus vary. Examples include rhamnose, isopropyl β-d-1-thiogalactopyranoside (IPTG), and 1-arabinose, though other inducing agents are compatible with the disclosed methods. The concentration and/or volume of inducing agents depends on the cell line and strain used, as well as the desired induction time and protein 20 yield. Induction conditions, such as temperature, percentage $CO_2$, humidity, and induction time additionally vary based on cell line, strain, and desired protein 20 yield. For example, induction times vary from a few hours to 24 hours, but in many embodiments are between about 18 hours to 20 hours.

Induction of protein 20 expression shifts culture conditions in LDPE bag 10 from those favoring bacterial cell growth to those favoring protein 20 expression within cells 12. Following the induction period, cells 12 are harvested, pelleted, and lysed as described for plasmid DNA production embodiments and shown in FIG. 17, step 160. The separation and purification of the expressed protein 20 from other host cellular components is undertaken using protocols known in the art and commercial kits and reagents. In instances where the recombinant protein 20 includes a tag, this tag is available to assist in the separation of the expressed protein 20 from cellular DNA, RNA, and endogenous proteins. For example, histidine tags are often used with recombinant proteins 20 such that they bind to chromatography columns with immobilized metal ions, including nickel, cobalt and copper, or to anti-histidine antibodies. These recombinant proteins 20 are then eluted from the column. The purity of the expressed protein 20 is evaluated using methods such as SDS-PAGE and Western blotting techniques.

The disclosed method of bacterial growth in LDPE bags 10 results in equal or greater bacterial growth than conventional shake flasks under equivalent growth conditions. Plasmid DNA 18 and/or recombinant molecules produced by bacterial host cells 12 grown using the LDPE-based growth methods is of equal or greater purity relative to that generated using flask-based methods. Therefore, the disclosed methods offer a less-expensive, sterile alternative to shake flask-based bacterial cell growth for plasmid DNA 18 and recombinant molecule production. The disclosed method is particularly advantageous when quantities of about 0.5 mg to 2 mg of plasmid DNA 18 are desired. Comparisons between flasks and LDPE bag 10 methods, as well as growth condition optimization, are detailed in the following examples.

Producing plasmids 18 in LDPE bags 10 has positive applications to personalized gene therapy and molecular biology research. LDPE bags 10 are economical and require less energy than flasks during cell incubation by virtue of LDPE bags 10 being less expensive and requiring less space for equivalent cell growth. LDPE bags 10 are also less expensive to transport than conventional flasks and can be closed during bacterial growth to prevent cross contamination and environmental contamination. Use of LDPE bags 10 for growth of hosts for plasmid DNA 18 production allows a reduction in the cost of gene therapy and general molecular biology applications.

Figure 2:
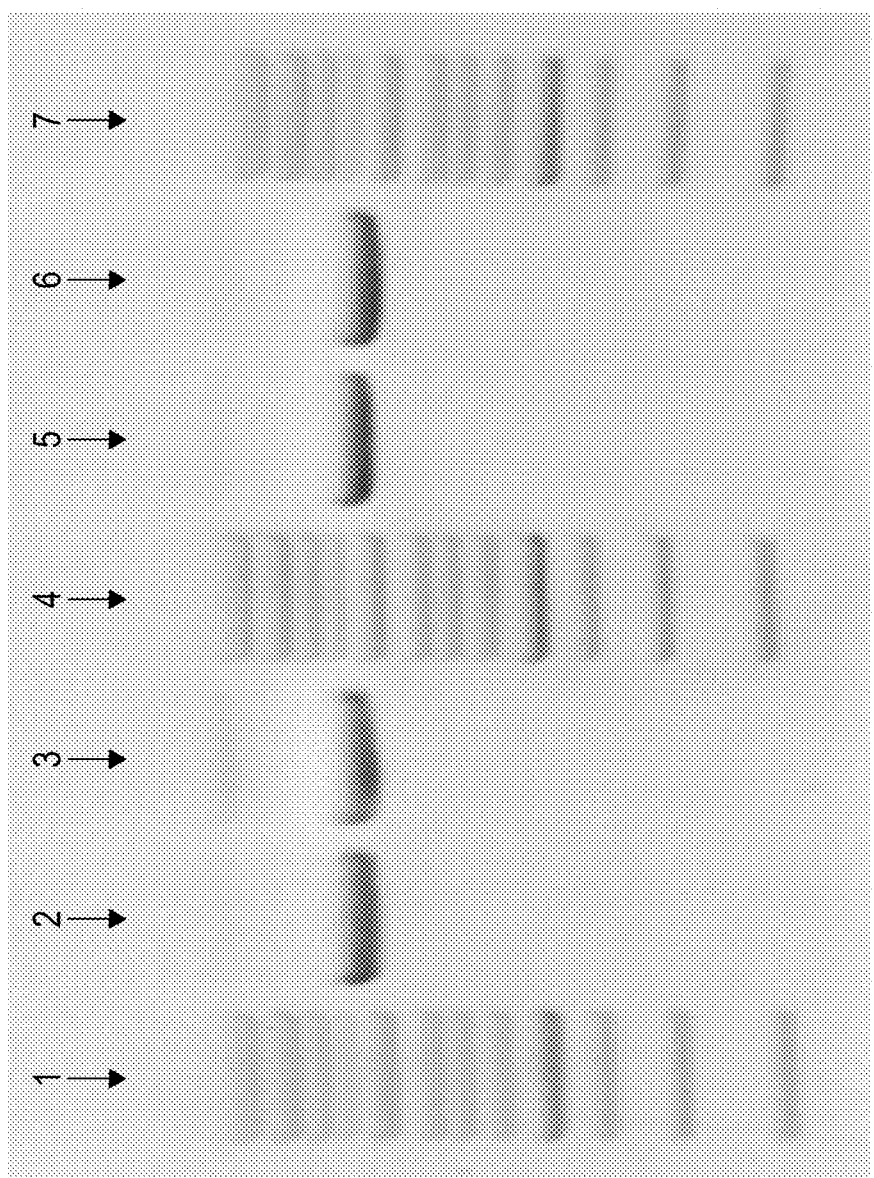
FIG. 2 is an image depicting plasmid DNA generated using the disclosed method of bacterial growth in LDPE bags, as well as plasmid DNA produced using plastic flasks and glass flasks for bacterial growth, and subjected to gel electrophoresis.

In FIGS. 1 and 2, bacterial growth and plasmid DNA purity, respectively, are compared after bacterial host cells are grown using traditional shake flasks or using LDPE bags of the present invention. FIG. 3A through FIG. 12 illustrate bacterial growth and/or plasmid DNA purity using a variety of growth conditions and different plasmids with traditional shake flasks or LDPE bags. FIG. 13 through FIG. 16 illustrate bacterial growth and/or recombinant protein expression using a variety of growth conditions with traditional shake flasks or LDPE bags. FIG. 17 is a flow chart showing the methods of bacterial growth in LDPE bags 10 for plasmid DNA 18 or protein 20 expression.

Example 1

Plasmids: A new plasmid (SUPERGLO) that constitutively expresses high levels of GFP (green fluorescent protein) under the control of a bacterial promoter was created using pGLO (Biorad, Hercules Calif.) in XL1-Red *E. coli* cells, which lack DNA repair mechanisms. Point mutations introduced into pGLO disrupted the vector's arabinose operon. A mutated plasmid library was transformed into DH5α, and a high-GFP expressing colony, in the absence of arabinose, was selected. A cell bank was made and used for all growth experiments. SUPERGLO is a model plasmid that enables a real-time quality control step of checking for florescence at any time with a UV light.

Low-density polyethylene bags: An assortment of LDPE bags were purchased and tested for gas permeability by growing SUPERGLO-containing *E. coli* cells in them. Types and sizes tested included 1 gallon freezer bags, 1 gallon storage bags, quart size freezer bags, quart size storage bags, sandwich bags, and extra-large sandwich bags. Volume of media varied with 50 mL, 250 mL and 1 L volumes of LB media used. The volume of media for extra-large sandwich bags was 50 mL. Bags were tested for sterility by filling them with sterile LB media and incubating at 37° C. for 24 hours. When tested with SUPERGLO, bags were filled with a set amount of LB media containing 100 μg/ml of carbenicillin. Bags were grown in a conventional incubated shaker at set agitation rate and temperature. Growth in bags at 37° C. and 70 rpm was compared to conventional shake flask growth at 37° C. and 250 rpm.

SUPERGLO: Plasmid DNA was subsequently purified using commercially available anion-exchange kits (Qiagen, Germantown Mass.). Plasmid quality was determined by agarose gel electrophoresis.

Sterility results: No microbial contamination was observed during the proof-of-concept experiments. Commercially available LDPE bags are sufficiently sterile for bacterial host cell growth. The LDPE bags can be further sterilized with gamma radiation. The media used in such bags can also be sterilized with gamma radiation and/or by filter sterilization.

Bacterial growth trials: Twenty growth trials were conducted (n=20) and demonstrated that thinner XL sandwich bags allowed for the highest growth rates. LDPE bags were comparable to conventional shake flasks in their ability to support SUPERGLO plasmid production. GFP strongly fluoresced in all systems.

Quantitative results: Multiple samples were taken to determine quantitative results. Tests included the final $OD_{600}$ of cultures, bacterial pellet weight of cultures, and the final plasmid yield produced.

Referring to FIG. 1, comparative growth curves for bacteria cultured in a plastic flask, a glass flask, and a LDPE bag are shown. $OD_{600}$ measurements were taken periodically throughout the growth of bacterial cells in each system. The media sample size was 2 L of LB soy media. As shown in FIG. 1, the LDPE bag system has faster growth than the traditional flask system.

Table 1 lists a comparison of the final $OD_{600}$ and DNA yield from a flask and LDPE bags. The media sample size was 50 mL of LB soy media. A higher $OD_{600}$ correlates with a higher concentration of bacteria in a culture.

| Growth Method | Final OD600 | DNA Yield (mg/L) |
| --- | --- | --- |
| Flask | 2.031 | 0.24 |
| XL Sand LDPB | 0.867 | 0.6 |
| 1 Gal LDPB | 0.27 | 0.32 |

The data in FIG. 2 demonstrates that the $OD_{600}$ measurement of host cell density with use of the LDPE bags is comparable to, or higher than, that obtained with use of flasks. The LDPE bags used were a small "sandwich"-sized LDPE bag and a large "gallon"-sized LDPE bag. Flasks were conventional 125 mL shake flasks. In each case, 50 mL of LB media was used. A number of separate experiments were performed and no significant difference in growth rate, plasmid yield or plasmid quality was found between glass and non-glass flasks. Lanes of the imaged gel, from left to right, represent 1: a DNA ladder of molecular weight standards, 2: plasmid DNA from bacteria grown in a first flask, 3: plasmid DNA from bacteria grown in a second flask, 4: a DNA ladder of molecular weight standards, 5: plasmid DNA from bacteria grown in a small, "sandwich"-sized LDPE bag, 6: plasmid DNA from bacteria grown in a large, "gallon"-sized LDPE bag, and 7: a DNA ladder of molecular weight standards.

Example 2

In this experiment, the growth of bacterial cells containing the plasmids in gas permeable LDPE bags is compared to their growth in 125 mL shake flasks. Identical conditions are used for comparison. The standard conditions include, unless indicated as varied: a growth temperature of 30° C., 34° C., or 37° C., an agitation rate of 250 rpm, RG growth media, kanamycin selection, an Endura® *E. coli* strain (Lucigen, Middleton, Wis.), and a gWiz™ GFP (green fluorescent protein) plasmid (Aldevron, Fargo, N. Dak.) with a CMV IE promoter, intron A, an artificial transcription terminator, and kanamycin resistance. LDPE bags were small, 6 inches by 9 inches bags.

About 10 mL of LB soy media with kanamycin was added to a 50 mL tube. An isolated colony of host cells containing the gWiz™ GFP plasmid from the plate were added to the tube using an inoculation loop. The tube was incubated at 37° C. with 250 rpm agitation for 5-7 hours until the culture was turbid. A 125 mL shake flask and small LDPE bag were each filled with 50 mL of RG media with kanamycin. A 100 μL aliquot of the starter culture was used to inoculate the shake flask and the LDPE bag. The flask and LDPE bag were incubated at the variable growth temperature with an agitation rate of 250 rpm for 18 hours. Interim samples were collected at different time points to measure $OD_{600}$ and pH. The surface temperature of the flask and LDPE bag were measured using an IR gun thermometer when the interim samples were collected.

Figure 3A:
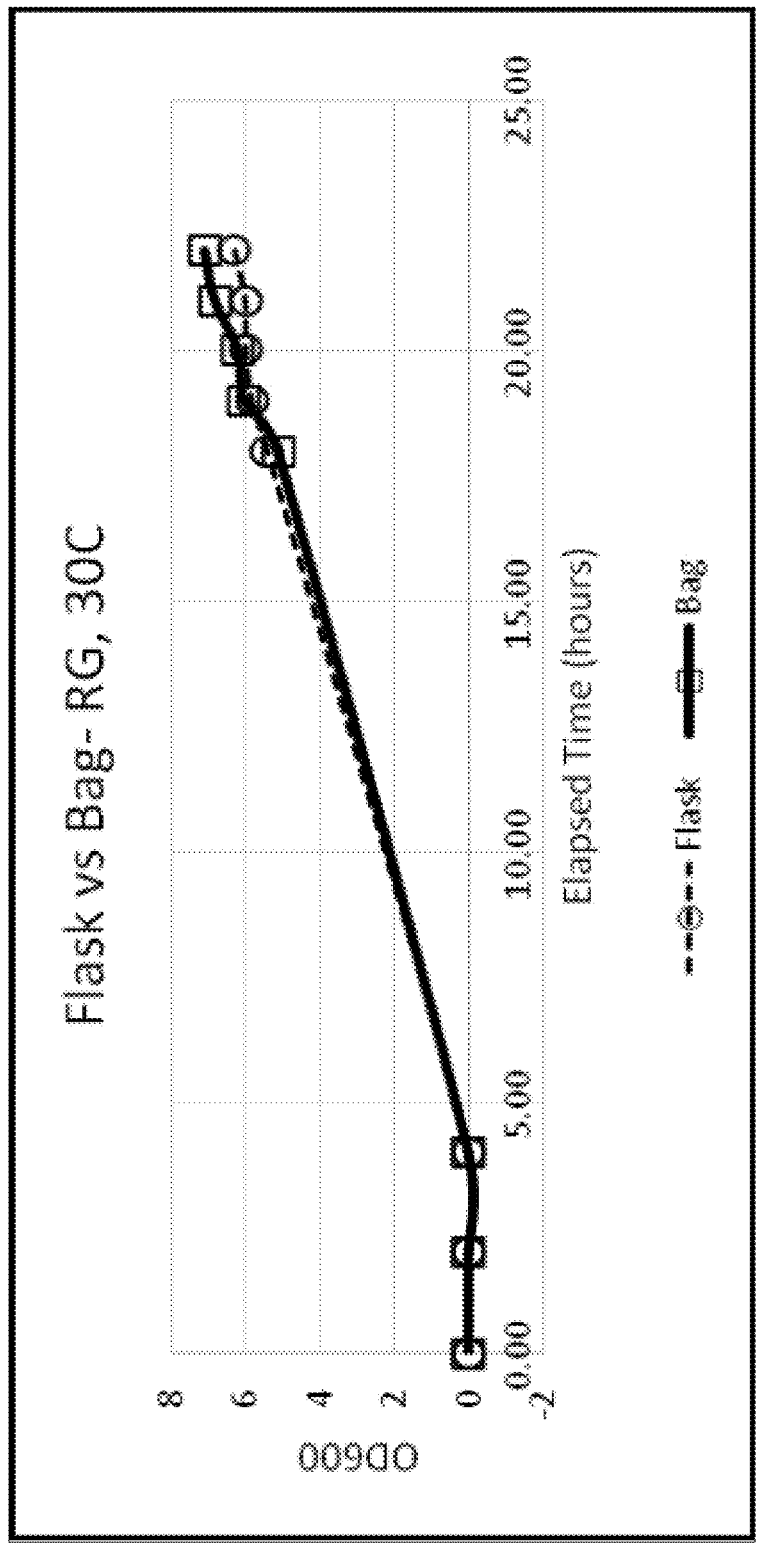
FIG. 3A is a graph illustrating the growth of bacteria in a LDPE bag according to the disclosed method compared to the growth of bacteria in a flask at a growth temperature of 30° C.
Figure 3B:
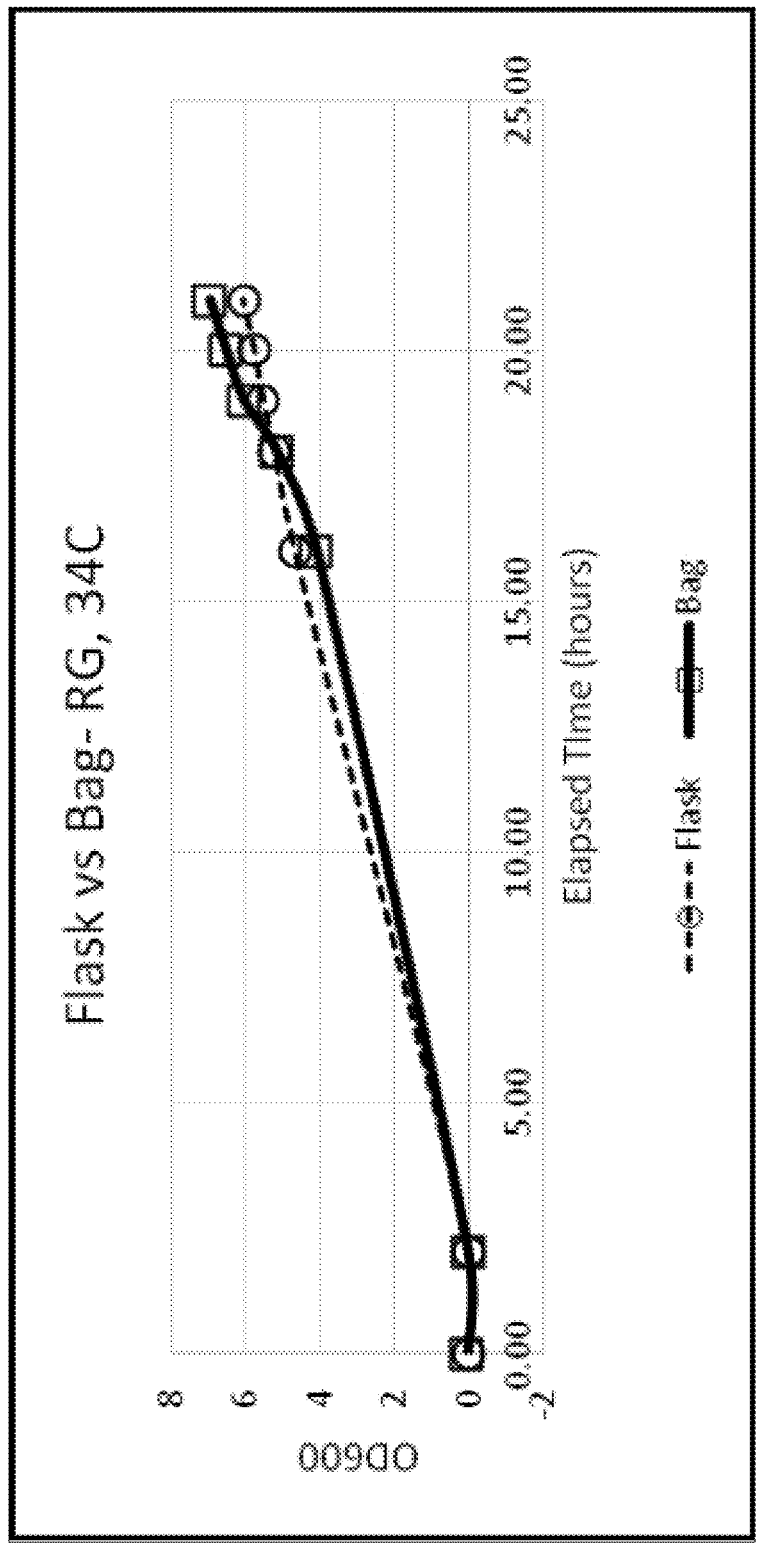
FIG. 3B is a graph illustrating the growth of bacteria in a LDPE bag according to the disclosed method compared to the growth of bacteria in a flask at a growth temperature of 34° C.
Figure 3C:
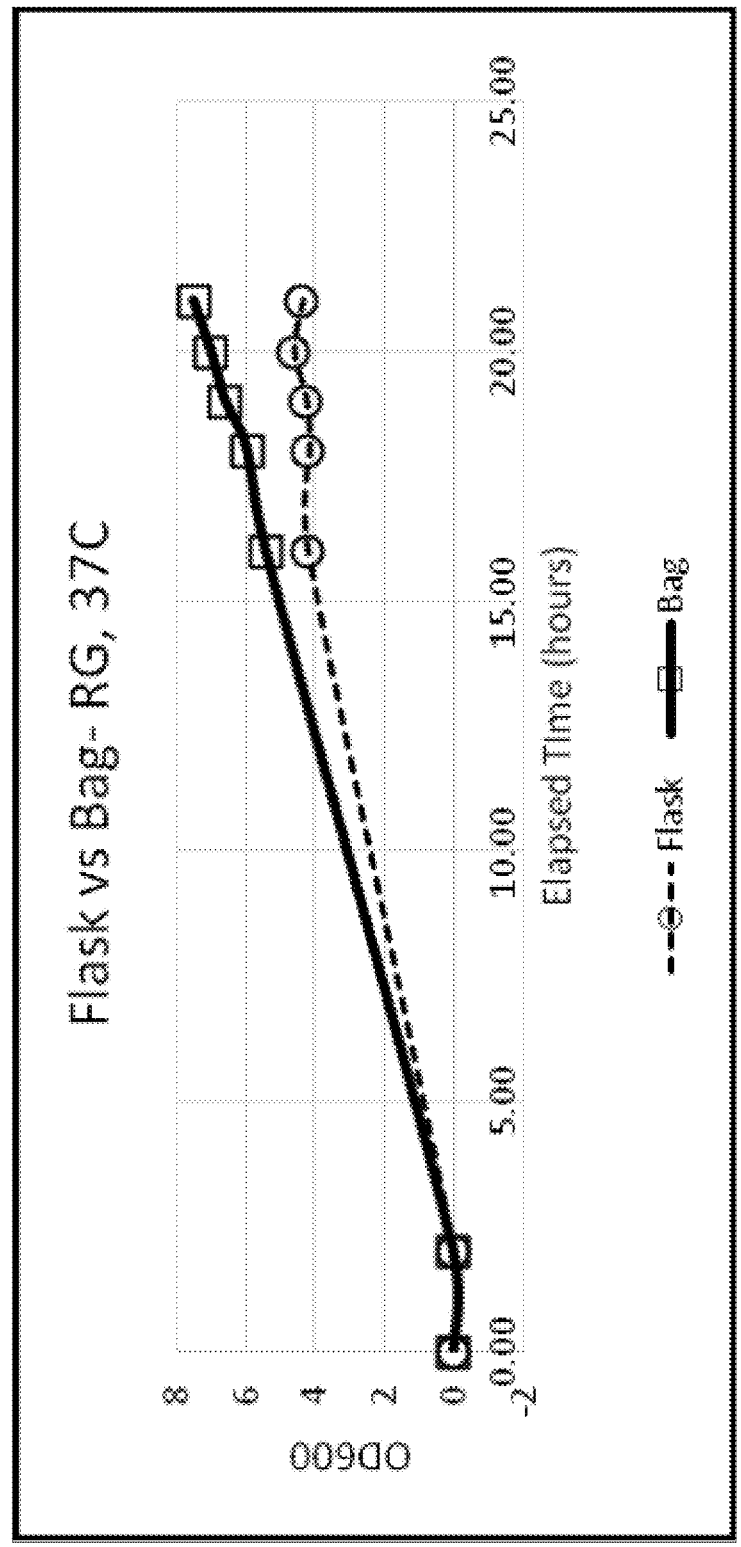
FIG. 3C is a graph illustrating the growth of bacteria in a LDPE bag according to the disclosed method compared to the growth of bacteria in a flask at a growth temperature of 37° C.

FIG. 3A, FIG. 3B, and FIG. 3C display the bacterial growth at varying growth temperatures for flask and LDPE bag methods. FIG. 3A shows growth at 30° C., FIG. 3B shows growth at 34° C., and FIG. 3C shows growth at 37° C. In each case, growth in an LDPE bag resulted in at least equal bacterial growth relative to growth in conventional flasks, with FIG. 3C showing faster bacterial growth in LDPE bags in comparison to bacterial growth in flasks.

Figure 4:
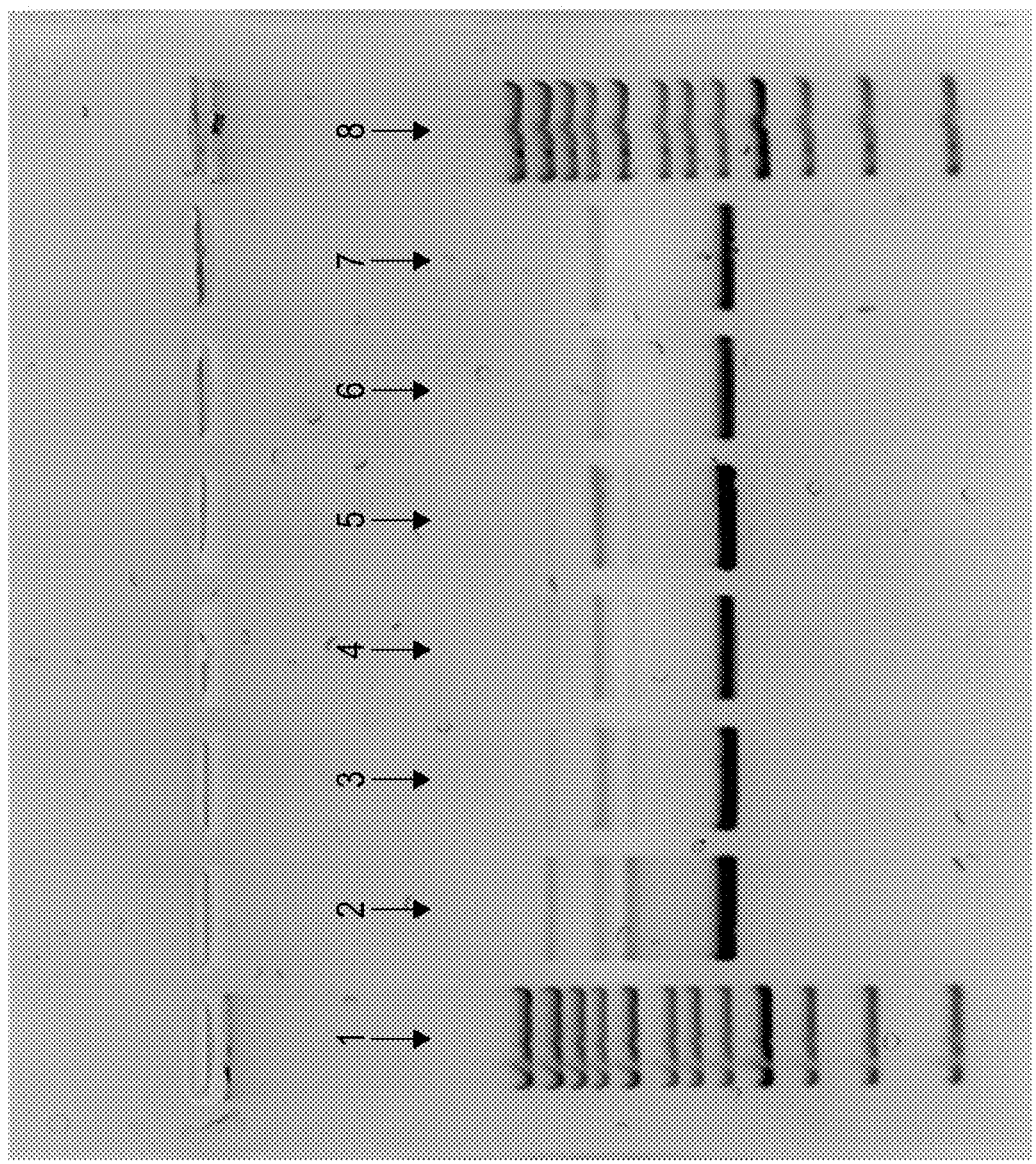
FIG. 4 is an image depicting plasmid DNA generated using the disclosed method of bacterial growth in LDPE bags, as well as plasmid DNA produced using a flask for bacterial growth at different growth temperatures, and subjected to gel electrophoresis.

Cells were then harvested by centrifugation at 10000×g and the weight of the cell pellet was measured. The cell pellet was resuspended and lysed to form a lysate, and the plasmid was purified from the lysate using commercially available anion-exchange kits. Results are shown in FIG. 4 with agarose gel electrophoresis, which separates DNA by molecular weight, used to show the relative amounts of plasmid DNA produced by growing in flasks and LDPE bags. Lanes of the imaged gel, from left to right, represent 1: a DNA ladder of molecular weight standards, 2: plasmid DNA from bacteria grown in a flask at 37° C., 3: plasmid DNA from bacteria grown in a LDPE bag at 37° C., 4: plasmid DNA from bacteria grown in a flask at 34° C., 5: plasmid DNA from bacteria grown in a LDPE bag at 34° C., 6: plasmid DNA from bacteria grown in a flask at 30° C., 7:

plasmid DNA from bacteria grown in a LDPE bag at 30° C., and 8: a DNA ladder of molecular weight standards. Production and purity of plasmid DNA from bacteria grown in LDPE bags was equal to or greater than that generated from bacteria grown in conventional shake flasks.

Example 3

In this experiment, the growth of bacterial cells containing plasmids in gas permeable LDPE bags of varying sizes is compared to their growth in 125 mL shake flasks. Identical conditions are used for comparison. The standard conditions include, unless indicated as varied: a growth temperature of 30° C., 34° C., or 37° C., an agitation rate of 200 rpm or 300 rpm, RG growth media, kanamycin selection, an Endura® E. coli strain (Lucigen, Middleton, Wis.), and a gWiz™ GFP plasmid (Aldevron, Fargo, N. Dak.) with a CMV IE promoter, intron A, an artificial transcription terminator, and kanamycin resistance. LDPE bags were small (6 inches by 9 inches), medium (8 inches by 10 inches), or large (12 inches by 12 inches).

Approximately 10 mL of LB soy media with kanamycin was added to a 50 mL tube. An isolated colony of host cells containing the gWiz™ GFP plasmid from the plate were added to this tube using an inoculation loop. The tube was incubated at a 37° C. with 250 rpm agitation for 5-7 hours until the culture was turbid. A 125 mL shake flask and small, medium, and large LDPE bags were each filled with 50 mL of the RG media with kanamycin. A 100 µL aliquot of the starter culture was used to inoculate the shake flask and the LDPE bags. The flask and LDPE bags were incubated at the variable growth temperature with an agitation rate of 200 rpm or 300 rpm for 18 hours. Interim samples were collected at different time points to measure $OD_{600}$ and pH. The surface temperature of the flask and LDPE bags were measured using an IR gun thermometer when the interim samples were collected.

Figure 5A:
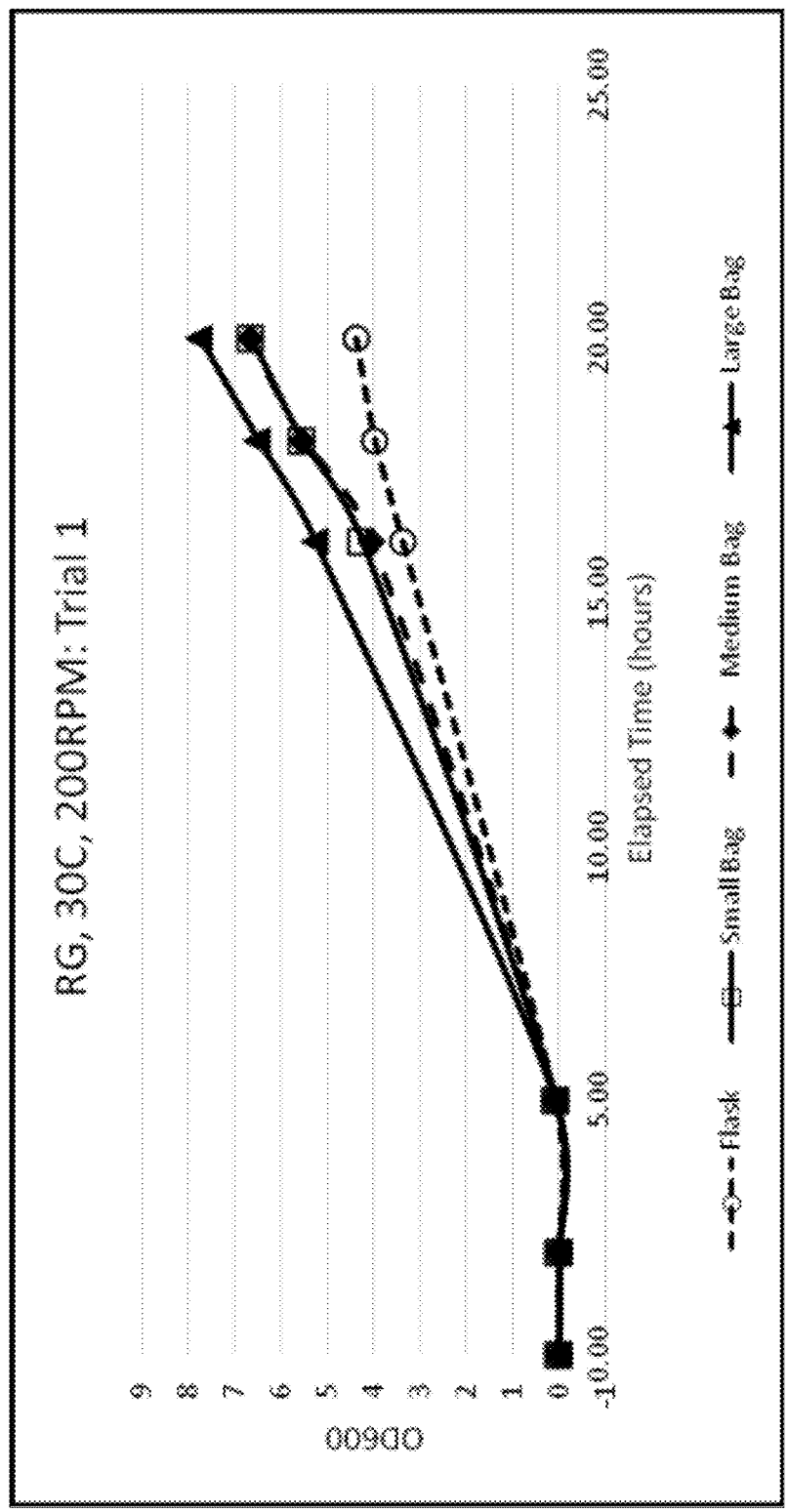
FIG. 5A is a graph illustrating the growth of bacteria in differently-sized LDPE bags according to the disclosed method compared to the growth of bacteria in a flask in a first trial at a growth temperature of 30° C.
Figure 5B:
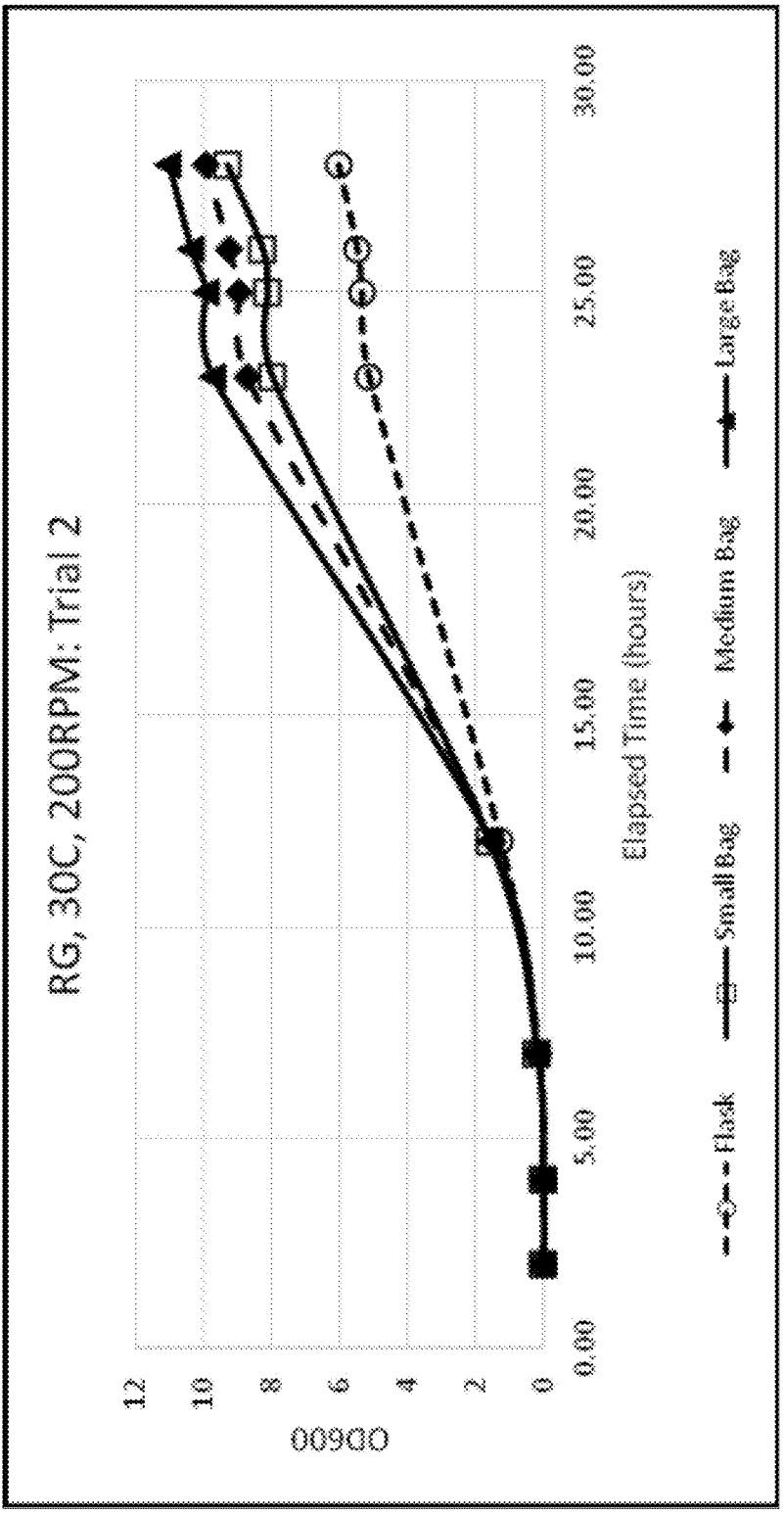
FIG. 5B is a graph illustrating the growth of bacteria in differently-sized LDPE bags according to the disclosed method compared to the growth of bacteria in a flask in a second trial at a growth temperature of 30° C.
Figure 5C:
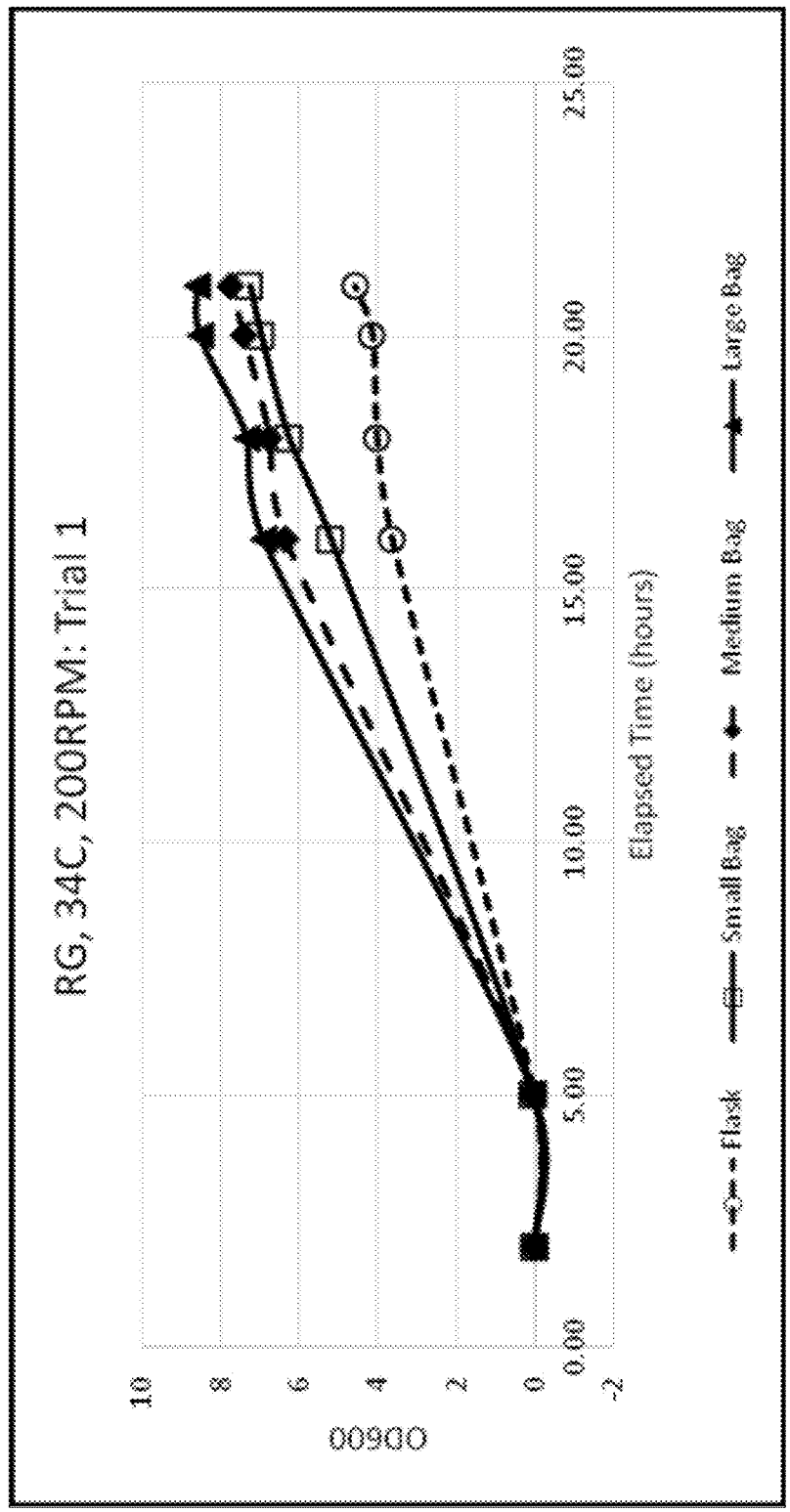
FIG. 5C is a graph illustrating the growth of bacteria in differently-sized LDPE bags according to the disclosed method compared to the growth of bacteria in a flask in a first trial at a growth temperature of 34° C.
Figure 5D:
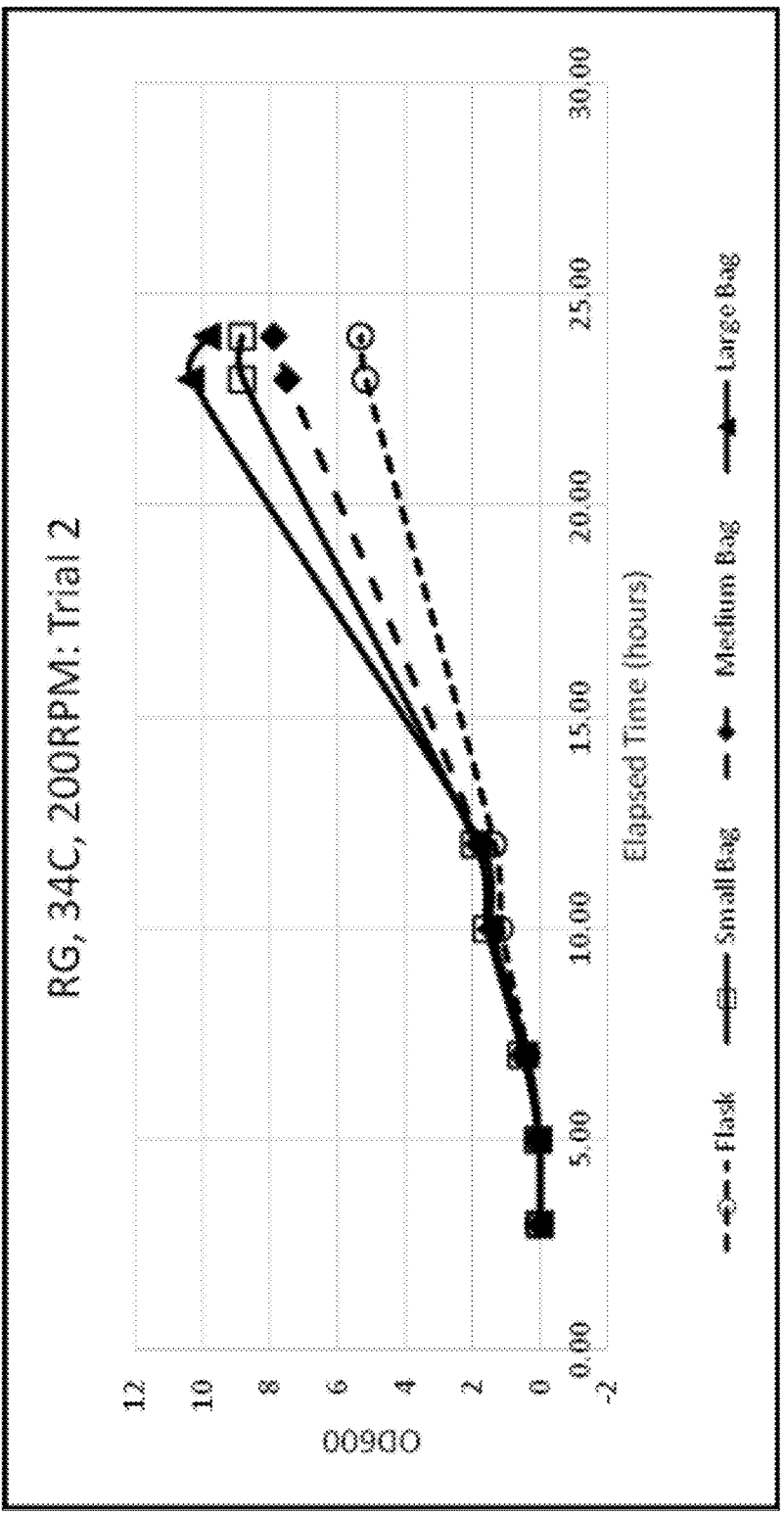
FIG. 5D is a graph illustrating the growth of bacteria in differently-sized LDPE bags according to the disclosed method compared to the growth of bacteria in a flask in a second trial at a growth temperature of 34° C.
Figure 5E:
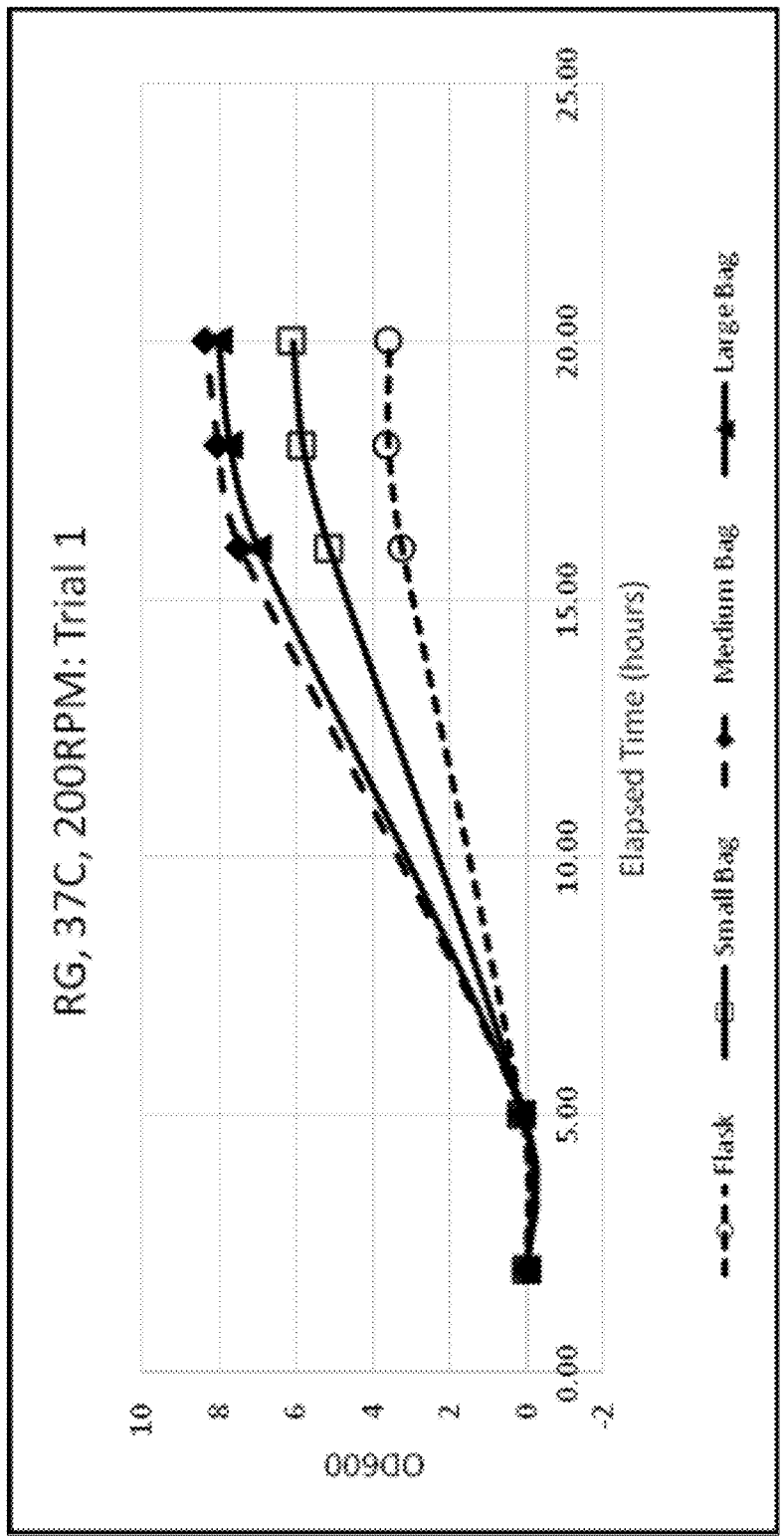
FIG. 5E is a graph illustrating the growth of bacteria in differently-sized LDPE bags according to the disclosed method compared to the growth of bacteria in a flask in a first trial at a growth temperature of 37° C.
Figure 5F:
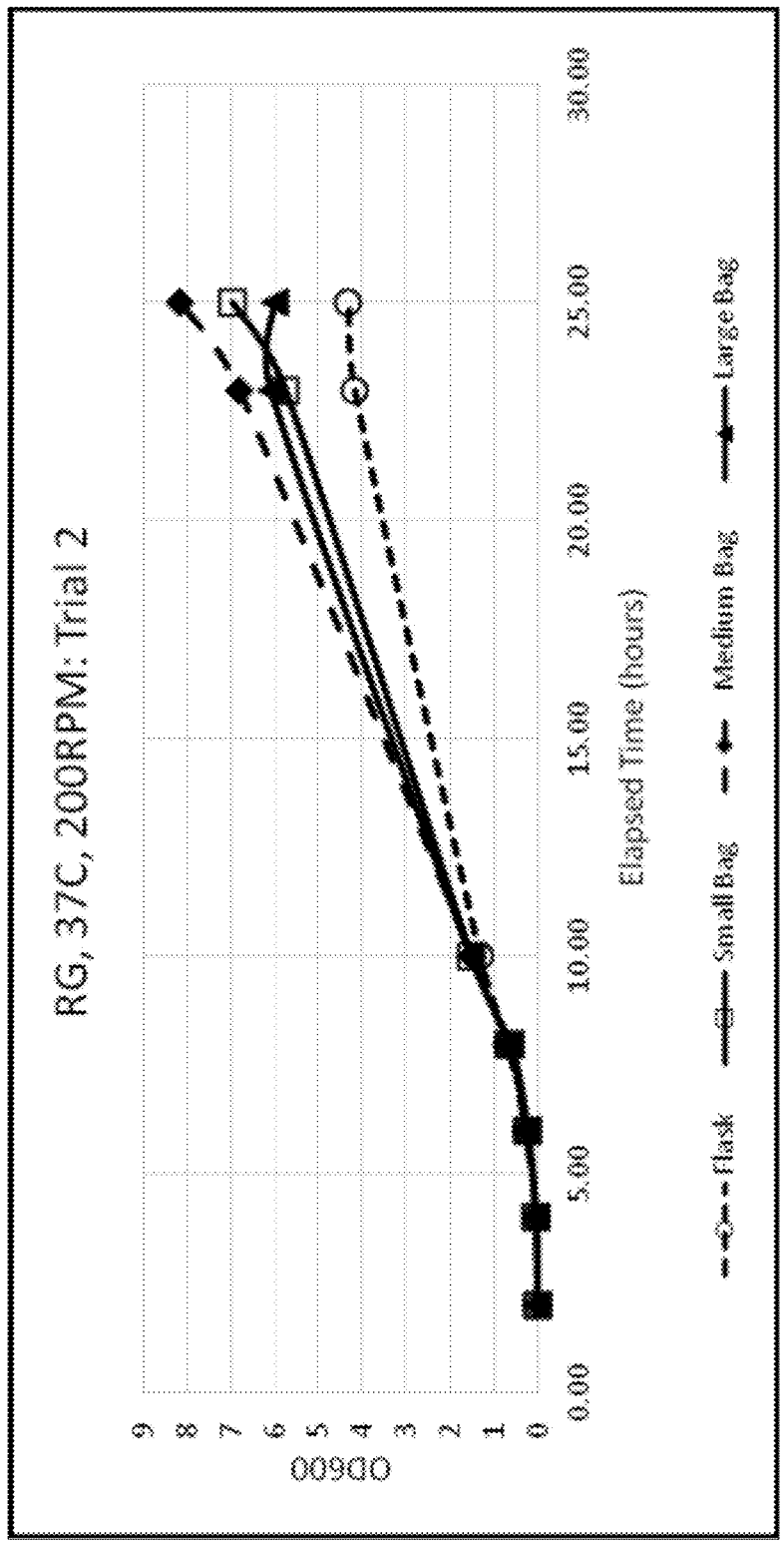
FIG. 5F is a graph illustrating the growth of bacteria in differently-sized LDPE bags according to the disclosed method compared to the growth of bacteria in a flask in a second trial at a growth temperature of 37° C.

FIGS. 5A-F record bacterial growth at varying temperatures in flasks and LDPE bags. FIG. 5A shows growth in a first trial at 30° C. and 200 rpm, FIG. 5B shows growth in a second trial at 30° C. and 200 rpm, FIG. 5C shows growth in a first trial at 34° C. and 200 rpm, FIG. 5D shows growth in a second trial at 34° C. and 200 rpm, FIG. 5E shows growth in a first trial at 37° C. and 200 rpm, and FIG. 5F shows growth in a second trial at 37° C. and 200 rpm. In each case, growth in LDPE bags resulted in faster bacterial growth than growth in conventional flasks. Higher temperatures and growth in larger LDPE bags resulted in increased bacterial host cell growth.

Figure 7A:
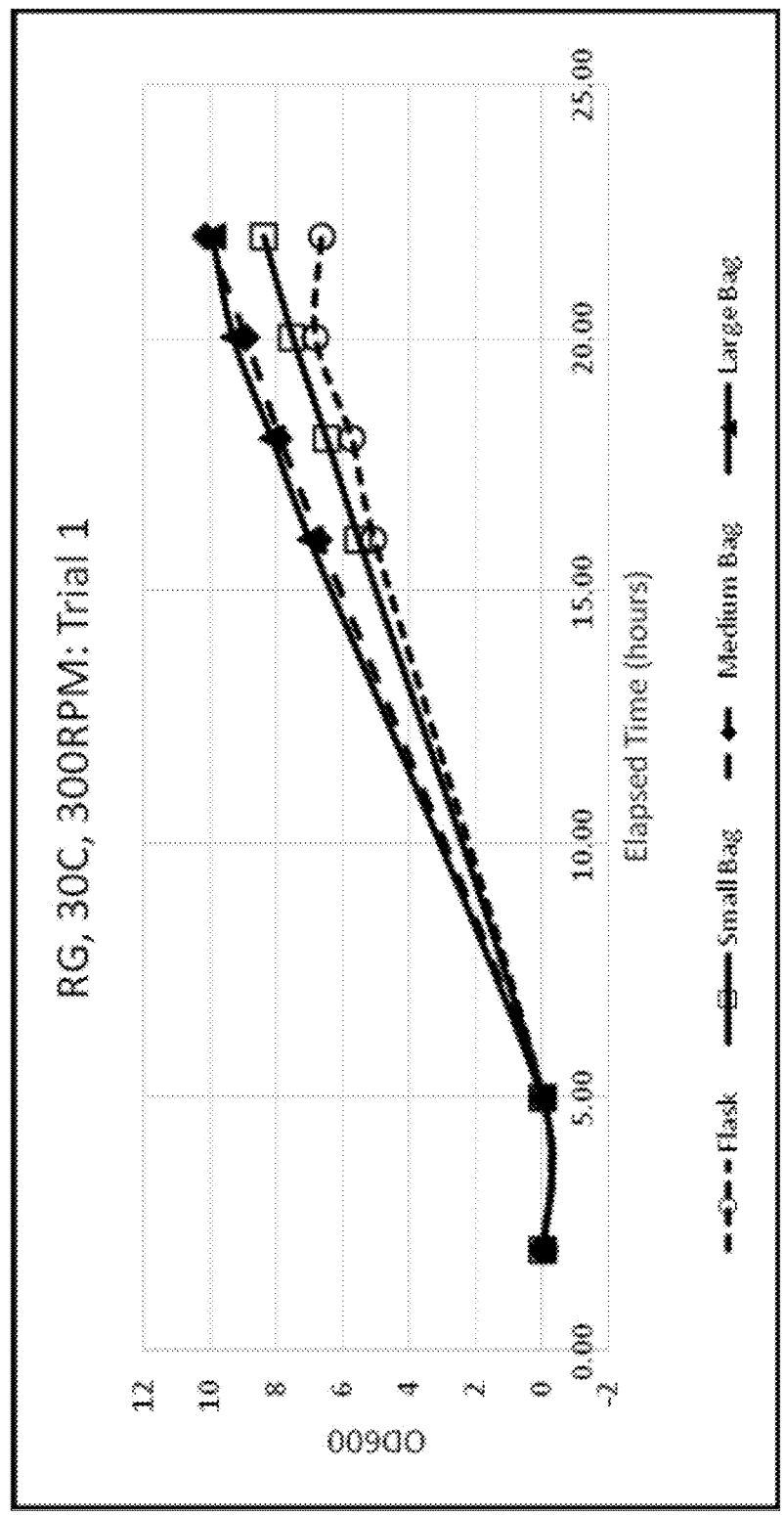
FIG. 7A is a graph illustrating the growth of bacteria in differently-sized LDPE bags according to the disclosed method compared to the growth of bacteria in a flask in a first trial at a growth temperature of 30° C.
Figure 7B:
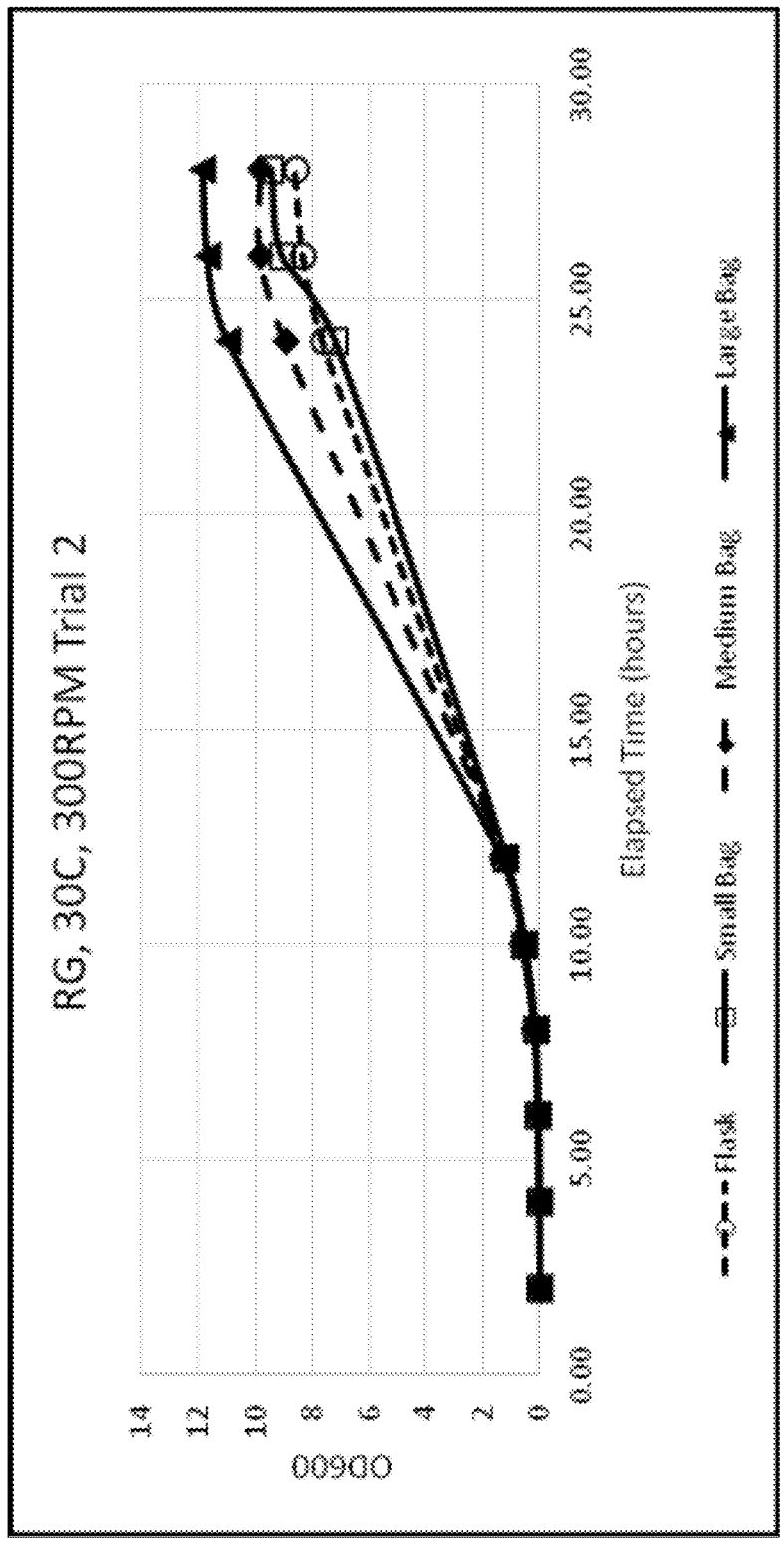
FIG. 7B is a graph illustrating the growth of bacteria in differently-sized LDPE bags according to the disclosed method compared to the growth of bacteria in a flask in a second trial at a growth temperature of 30° C.
Figure 7C:
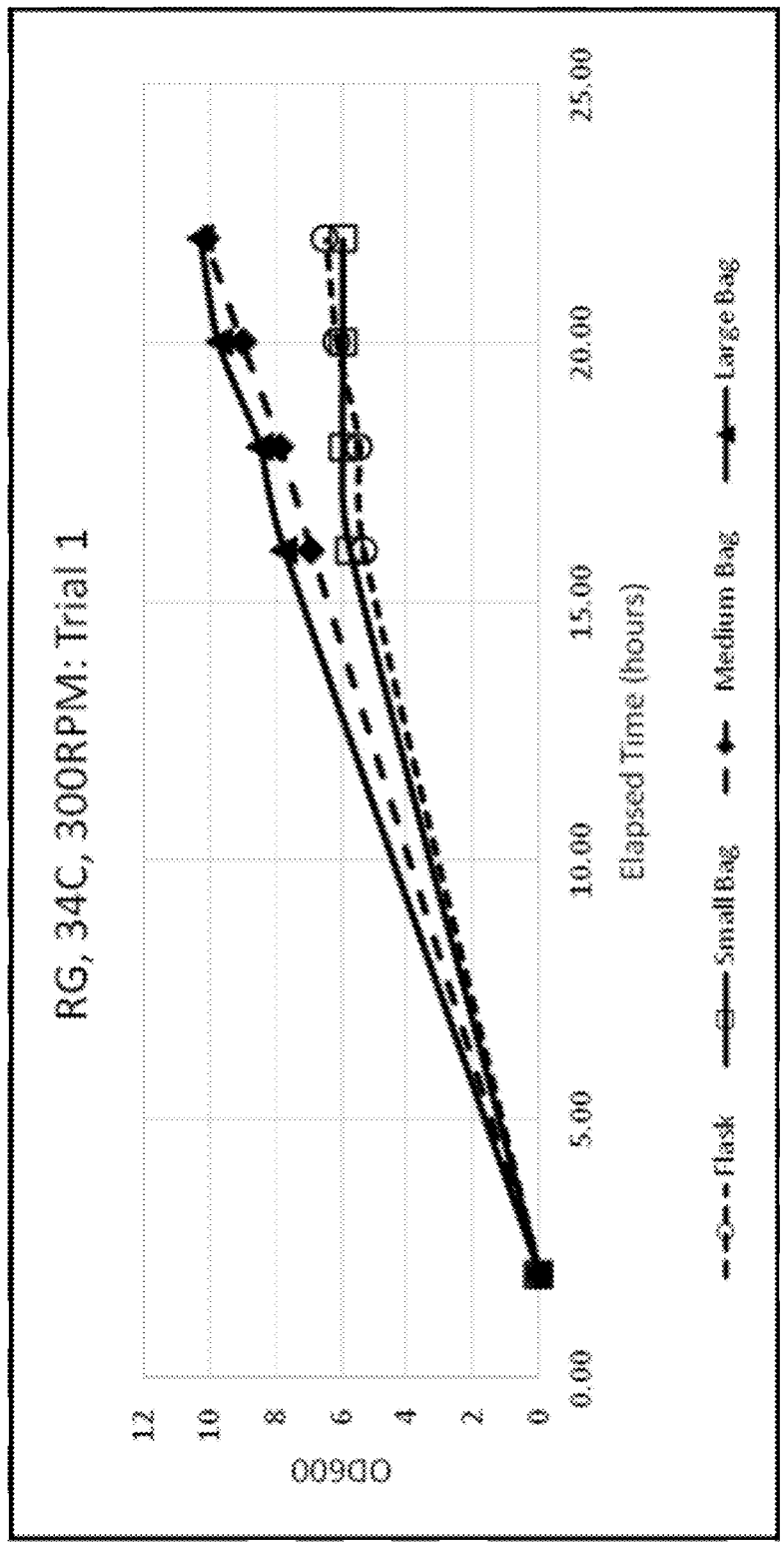
FIG. 7C is a graph illustrating the growth of bacteria in differently-sized LDPE bags according to the disclosed method compared to the growth of bacteria in a flask in a first trial at a growth temperature of 34° C.
Figure 7D:
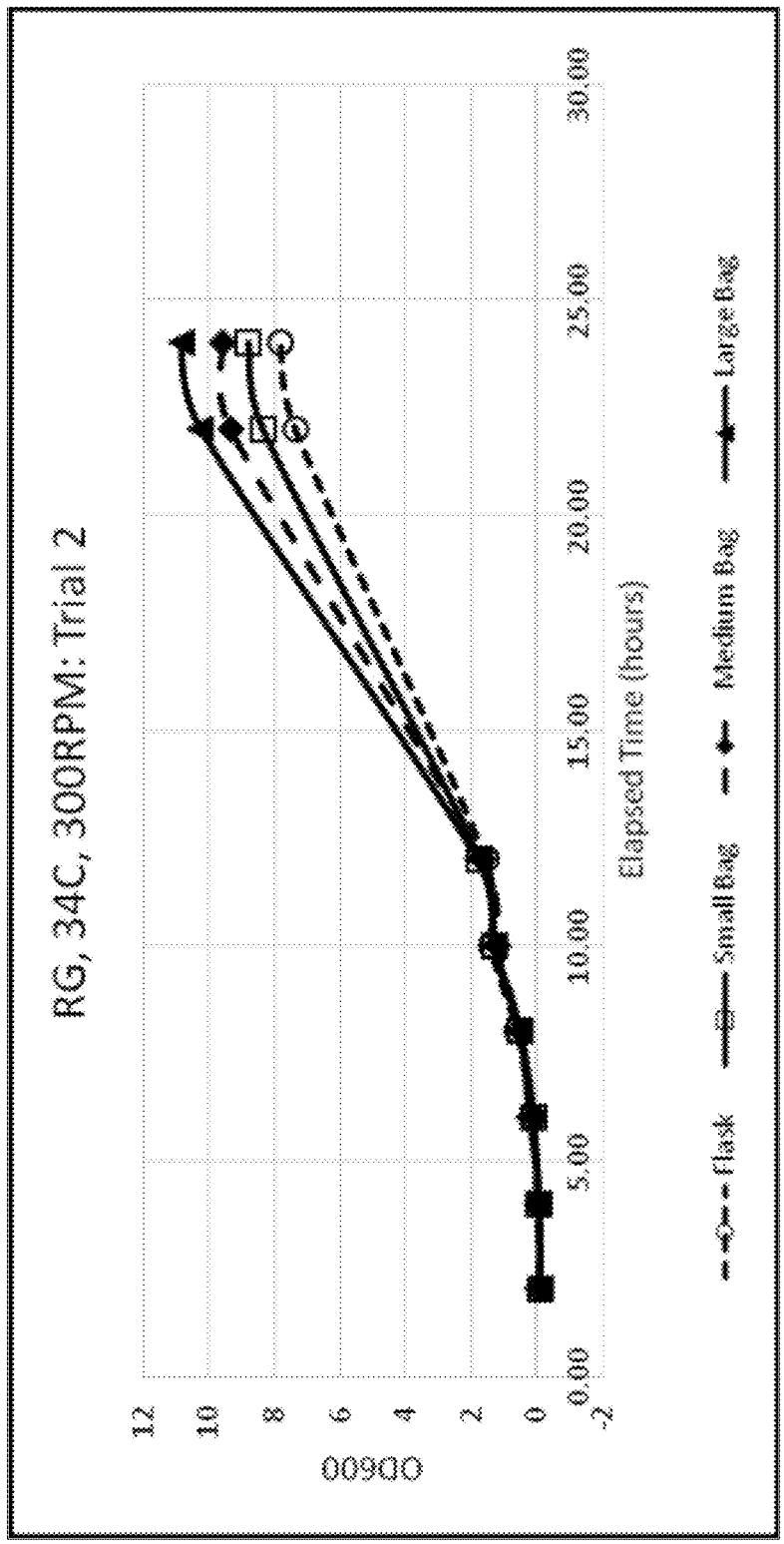
FIG. 7D is a graph illustrating the growth of bacteria in differently-sized LDPE bags according to the disclosed method compared to the growth of bacteria in a flask in a second trial at a growth temperature of 34° C.
Figure 7E:
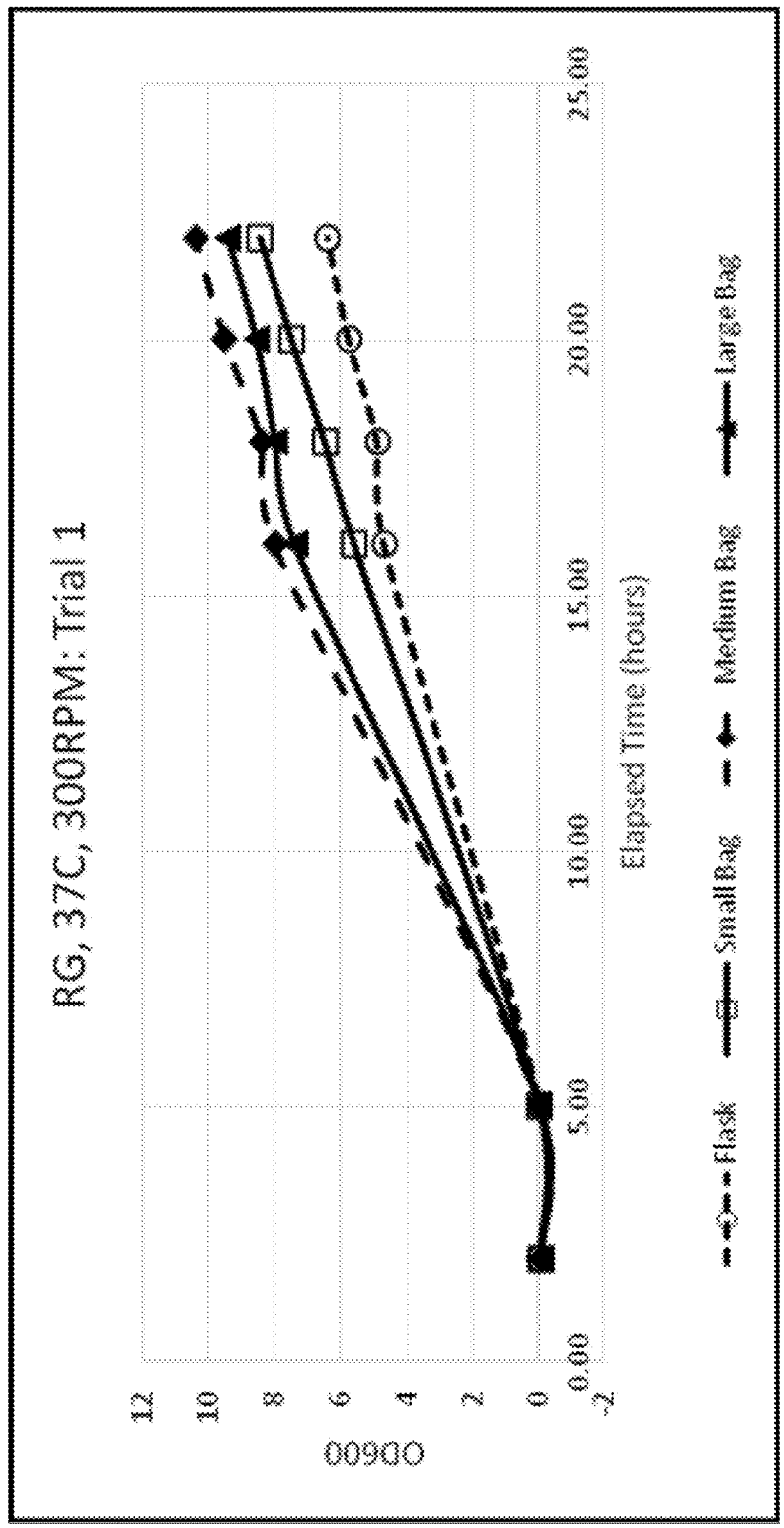
FIG. 7E is a graph illustrating the growth of bacteria in differently-sized LDPE bags according to the disclosed method compared to the growth of bacteria in a flask in a first trial at a growth temperature of 37° C.
Figure 7F:
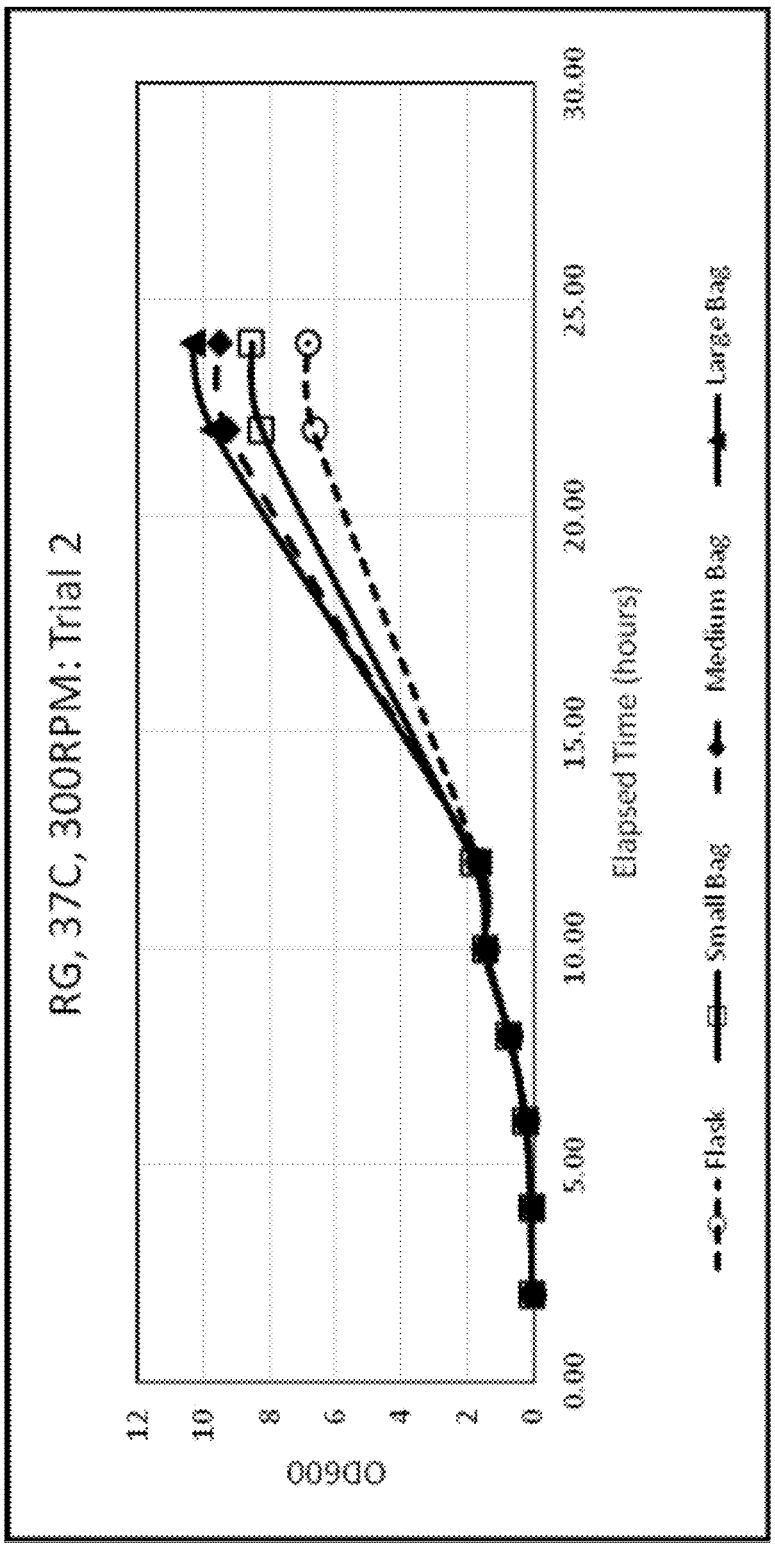
FIG. 7F is a graph illustrating the growth of bacteria in differently-sized LDPE bags according to the disclosed method compared to the growth of bacteria in a flask in a second trial at a growth temperature of 37° C.

In FIGS. 7A-F record bacterial growth at varying temperatures in flasks and LDPE bags. FIG. 7A shows growth in a first trial at 30° C. and 300 rpm, FIG. 7B shows growth in a second trial at 30° C. and 300 rpm, FIG. 7C shows growth in a first trial at 34° C. and 300 rpm, FIG. 7D shows growth in a second trial at 34° C. and 300 rpm, FIG. 7E shows growth in a first trial at 37° C. and 300 rpm, and FIG. 7F shows growth in a second trial at 37° C. and 300 rpm. In each case, growth in LDPE bags resulted in faster bacterial growth than growth in conventional flasks. Higher temperatures and growth in larger LDPE bags generally resulted in increased bacterial host cell growth.

Figure 6A:
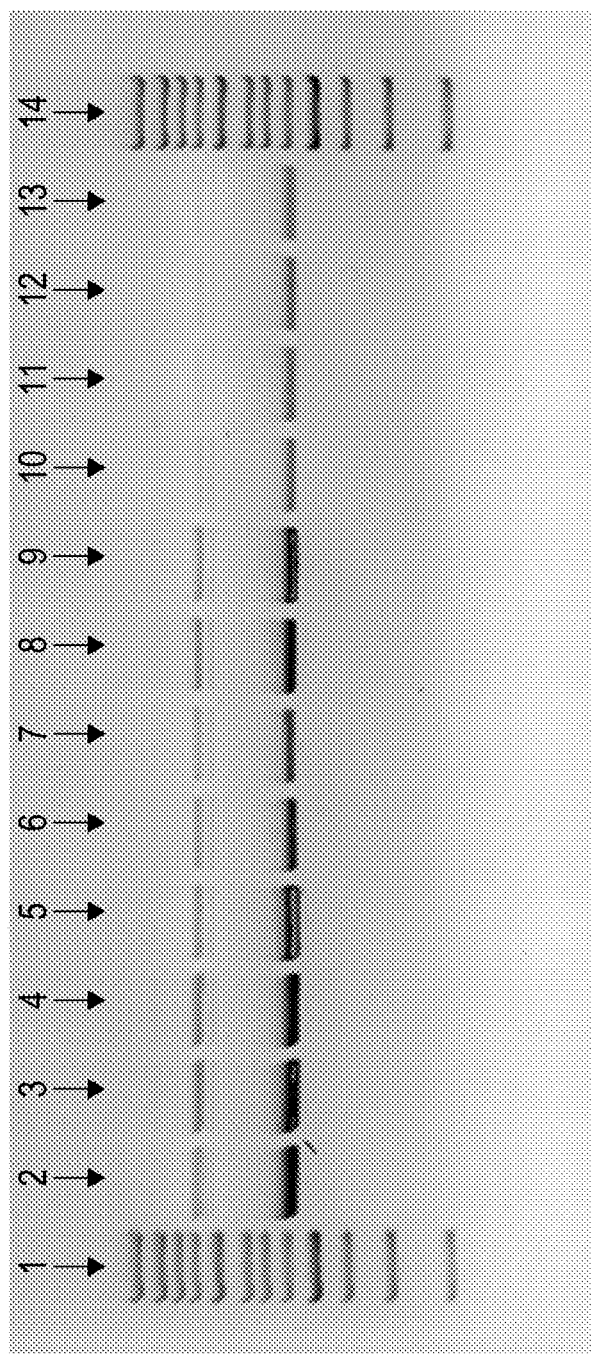
FIG. 6A is an image depicting plasmid DNA generated using the disclosed method of bacterial growth in differently-sized LDPE bags, as well as plasmid DNA produced using a flask for bacterial growth at different growth temperatures in a first trial, and subjected to gel electrophoresis.

Cells were harvested by centrifugation at 10000×g and the weight of the cell pellet was measured. The cell pellet was resuspended and lysed to form a lysate and the plasmid DNA was purified from the lysate using commercially available anion-exchange kits. Plasmid DNA is visualized in FIGS. 6A and 6B by agarose gel electrophoresis, which shows the relative amount and purity of plasmid DNA produced using flasks and LDPE bags for growth of bacterial cells. In FIG. 6A, an image depicting gel electrophoresis of plasmid DNA generated using the disclosed method of bacterial growth in differently-sized LDPE bags, as well as plasmid DNA produced using a flask for bacterial growth at different growth temperatures and at an agitation rate of 200 rpm in a first trial is shown. Lanes of the imaged gel, from left to right, represent 1: a DNA ladder of molecular weight standards, 2: plasmid DNA from bacteria grown in a flask at 37° C., 3: plasmid DNA from bacteria grown in a small, "sandwich"-sized LDPE bag at 37° C., 4: plasmid DNA from bacteria grown in a medium, "quart"-sized LDPE bag at 37° C., 5: plasmid DNA from bacteria grown in a large, "gallon"-sized LDPE bag at 37° C., 6: plasmid DNA from bacteria grown in a flask at 34° C., 7: plasmid DNA from bacteria grown in a small, "sandwich"-sized LDPE bag at 34° C., 8: plasmid DNA from bacteria grown in a medium, "quart"-sized LDPE bag at 34° C., 9: plasmid DNA from bacteria grown in a large, "gallon"-sized LDPE bag at 34° C., 10: plasmid DNA from bacteria grown in a flask at 30° C., 11: plasmid DNA from bacteria grown in a small, "sandwich"-sized LDPE bag at 30° C., 12: plasmid DNA from bacteria grown in a medium, "quart"-sized LDPE bag at 30° C., 13: plasmid DNA from bacteria grown in a large, "gallon"-sized LDPE bag at 30° C., and 14: a DNA ladder of molecular weight standards. The results generally show that higher temperatures lead to greater growth of bacteria, with 37° C. lanes having darker bands than 34° C. lanes and 30° C. lanes. Additionally, greater or equal growth of bacteria is shown in larger LDPE bag growth lanes relative to smaller LDPE bag growth lanes and flask growth lanes.

Figure 6B:
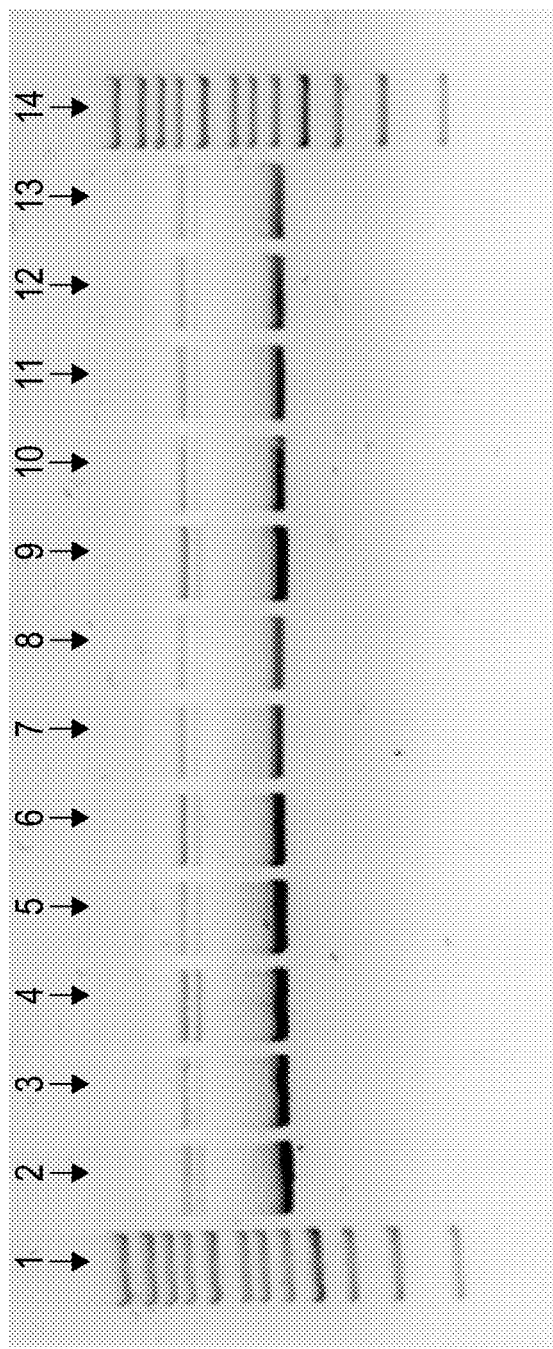
FIG. 6B is an image depicting plasmid DNA generated using the disclosed method of bacterial growth in differently-sized LDPE bags, as well as plasmid DNA produced using a flask for bacterial growth at different growth temperatures in a second trial, and subjected to gel electrophoresis.

In FIG. 6B, an image depicting gel electrophoresis of plasmid DNA generated using the disclosed method of bacterial growth in differently-sized LDPE bags, as well as plasmid DNA produced using a flask for bacterial growth at different growth temperatures and at an agitation rate of 200 rpm in a second trial is shown. Lanes of the imaged gel, from left to right, represent 1: a DNA ladder of molecular weight standards, 2: plasmid DNA from bacteria grown in a flask at 37° C., 3: plasmid DNA from bacteria grown in a small, "sandwich"-sized LDPE bag at 37° C., 4: plasmid DNA from bacteria grown in a medium, "quart"-sized LDPE bag at 37° C., 5: plasmid DNA from bacteria grown in a large, "gallon"-sized LDPE bag at 37° C., 6: plasmid DNA from bacteria grown in a flask at 34° C., 7: plasmid DNA from bacteria grown in a small, "sandwich"-sized LDPE bag at 34° C., 8: plasmid DNA from bacteria grown in a medium, "quart"-sized LDPE bag at 34° C., 9: plasmid DNA from bacteria grown in a large, "gallon"-sized LDPE bag at 34° C., 10: plasmid DNA from bacteria grown in a flask at 30° C., 11: plasmid DNA from bacteria grown in a small, "sandwich"-sized LDPE bag at 30° C., 12: plasmid DNA from bacteria grown in a medium, "quart"-sized LDPE bag at 30° C., 13: plasmid DNA from bacteria grown in a large, "gallon"-sized LDPE bag at 30° C., and 14: a DNA ladder of molecular weight standards. The results generally show that higher temperatures lead to greater growth of bacteria, with 37° C. lanes having darker bands than most 34° C. lanes and 30° C. lanes. Additionally, larger LDPE bags display darker and larger bands than medium and small LDPE bags and flasks at 37° C. and 34° C., indicating more growth of bacteria under these conditions.

Figure 8A:
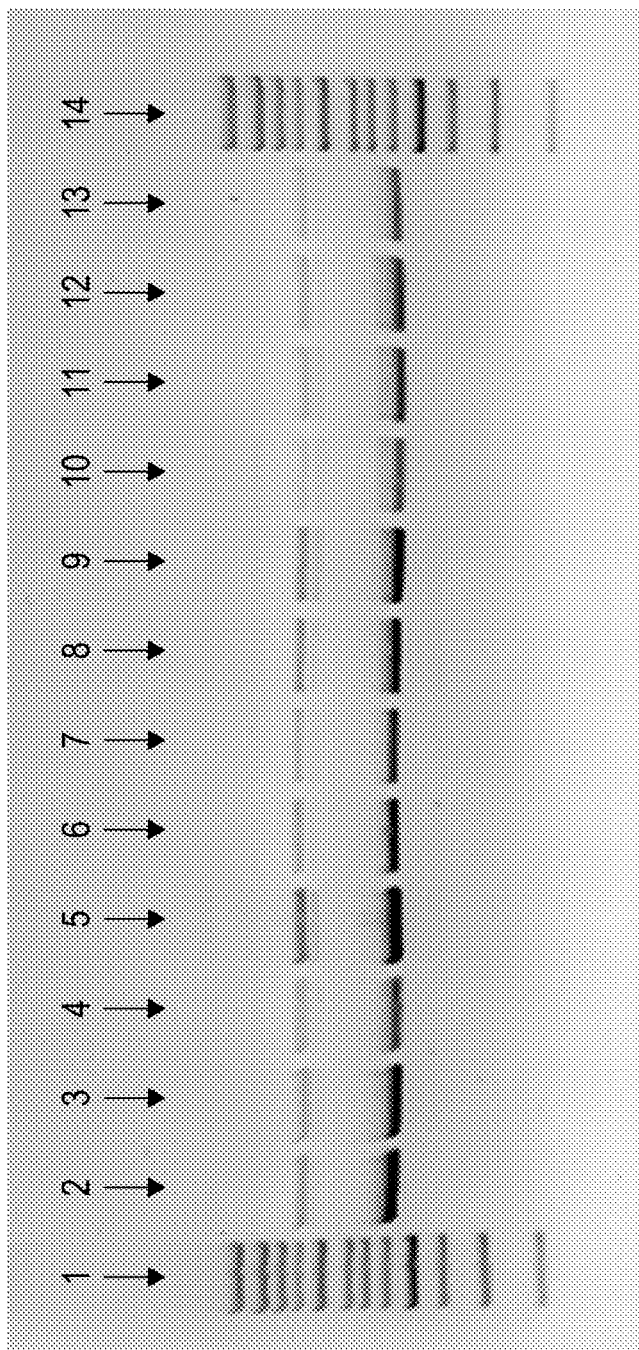
FIG. 8A is an image depicting plasmid DNA generated using the disclosed method of bacterial growth in differently-sized LDPE bags, as well as plasmid DNA produced using a flask for bacterial growth at different growth temperatures in a first trial, and subjected to gel electrophoresis.
Figure 8B:
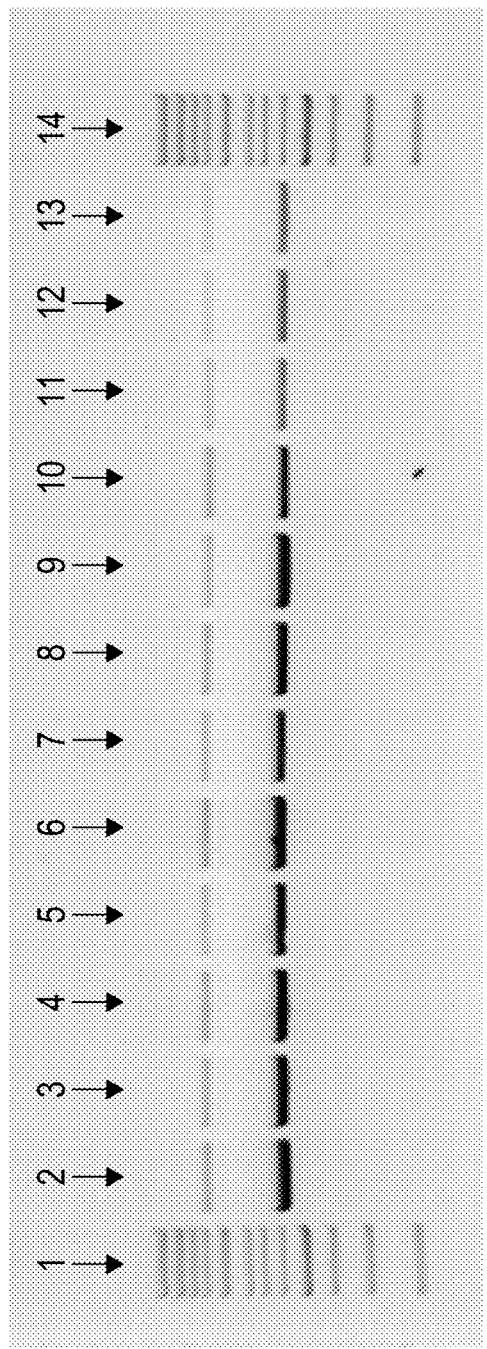
FIG. 8B is an image depicting plasmid DNA generated using the disclosed method of bacterial growth in differently-sized LDPE bags, as well as plasmid DNA produced using a flask for bacterial growth at different growth temperatures in a second trial, and subjected to gel electrophoresis.

In FIGS. 8A and 8B, agarose gel electrophoresis shows the relative amount and purity of plasmid DNA produced from bacterial cells grown in flasks and LDPE bags using an agitation rate of 300 rpm. FIG. 8A displays a first trial, where lanes of the gel, from left to right, represent 1: a DNA ladder of molecular weight standards, 2: plasmid DNA from bacteria grown in a flask at 37° C., 3: plasmid DNA from bacteria grown in a small, "sandwich"-sized LDPE bag at 37° C., 4: plasmid DNA from bacteria grown in a medium, "quart"-sized LDPE bag at 37° C., 5: plasmid DNA from bacteria grown in a large, "gallon"-sized LDPE bag at 37° C., 6: plasmid DNA from bacteria grown in a flask at 34° C., 7: plasmid DNA from bacteria grown in a small, "sandwich"-sized LDPE bag at 34° C., 8: plasmid DNA from bacteria grown in a medium, "quart"-sized LDPE bag at 34° C., 9: plasmid DNA from bacteria grown in a large, "gallon"-sized LDPE bag at 34° C., 10: plasmid DNA from bacteria grown in a flask at 30° C., 11: plasmid DNA from bacteria grown in a small, "sandwich"-sized LDPE bag at 30° C., 12: plasmid DNA from bacteria grown in a medium, "quart"-sized LDPE bag at 30° C., 13: plasmid DNA from bacteria grown in a large, "gallon"-sized LDPE bag at 30° C., and 14: a DNA ladder of molecular weight standards. The results generally show that higher temperatures lead to greater growth of bacteria, with 37° C. lanes having darker bands than most 34° C. lanes and 30° C. lanes. Additionally, larger LDPE bags display darker and larger bands than medium and small LDPE bags and flasks at 37° C. and 34° C., indicating more growth of bacteria under these conditions.

In FIG. 8B, plasmid DNA resulting from a second trial is displayed, in which lanes of the gel, from left to right, represent 1: a DNA ladder of molecular weight standards, 2: plasmid DNA from bacteria grown in a flask at 37° C., 3: plasmid DNA from bacteria grown in a small, "sandwich"-sized LDPE bag at 37° C., 4: plasmid DNA from bacteria grown in a medium, "quart"-sized LDPE bag at 37° C., 5: plasmid DNA from bacteria grown in a large, "gallon"-sized LDPE bag at 37° C., 6: plasmid DNA from bacteria grown in a flask at 34° C., 7: plasmid DNA from bacteria grown in a small, "sandwich"-sized LDPE bag at 34° C., 8: plasmid DNA from bacteria grown in a medium, "quart"-sized LDPE bag at 34° C., 9: plasmid DNA from bacteria grown in a large, "gallon"-sized LDPE bag at 34° C., 10: plasmid DNA from bacteria grown in a flask at 30° C., 11: plasmid DNA from bacteria grown in a small, "sandwich"-sized LDPE bag at 30° C., 12: plasmid DNA from bacteria grown in a medium, "quart"-sized LDPE bag at 30° C., 13: plasmid DNA from bacteria grown in a large, "gallon"-sized LDPE bag at 30° C., and 14: a DNA ladder of molecular weight standards. The results generally show that higher temperatures lead to greater growth of bacteria, with 37° C. lanes and 34° C. lanes displaying larger and darker bands than 30° C. lanes.

From the data shown in FIGS. 5-8, agitation rates at 300 rpm result in greater bacterial host cell growth than agitation rates of 200 rpm. Standard conditions for agitation of RG media-based bacterial cells is 400 rpm using shake flasks, so the present invention allows a reduction in agitation and potential energy savings for bacterial growth procedures.

Example 4

In this experiment, growth of plasmid-containing bacterial cells in gas permeable LDPE bags is compared to growth in 125 mL shake flasks. Identical conditions are used for comparison. The standard conditions include, unless indicated as varied: a growth temperature of 34° C., an agitation rate of 300 rpm, MY, TB, or LB growth media, kanamycin selection, an Endura® E. coli strain (Lucigen, Middleton, Wis.), and a gWiz' GFP plasmid (Aldevron, Fargo, N. Dak.) with a CMV IE promoter, intron A, an artificial transcription terminator, and kanamycin resistance. LDPE bags were medium size (about 8 inches by 10 inches).

Approximately 10 mL of LB soy media with kanamycin was added to a 50 mL tube. An isolated colony of host cells containing the gWiz' GFP plasmid from the plate were added to this tube using an inoculation loop. The tube was incubated at a 37° C. with 250 rpm agitation for 5-7 hours until the culture was turbid. A 125 mL shake flask and medium LDPE bag were each filled with 50 mL of the RG media with kanamycin. A 100 μL aliquot of the starter culture was used to inoculate the shake flask and the LDPE bag. The flask and LDPE bag were incubated at the 34° C. with an agitation rate of 300 rpm for 18 hours. Interim samples were collected at different time points to measure $OD_{600}$ and pH. The surface temperature of the flask and LDPE bag were measured using an IR gun thermometer when the interim samples were collected.

Figure 9A:
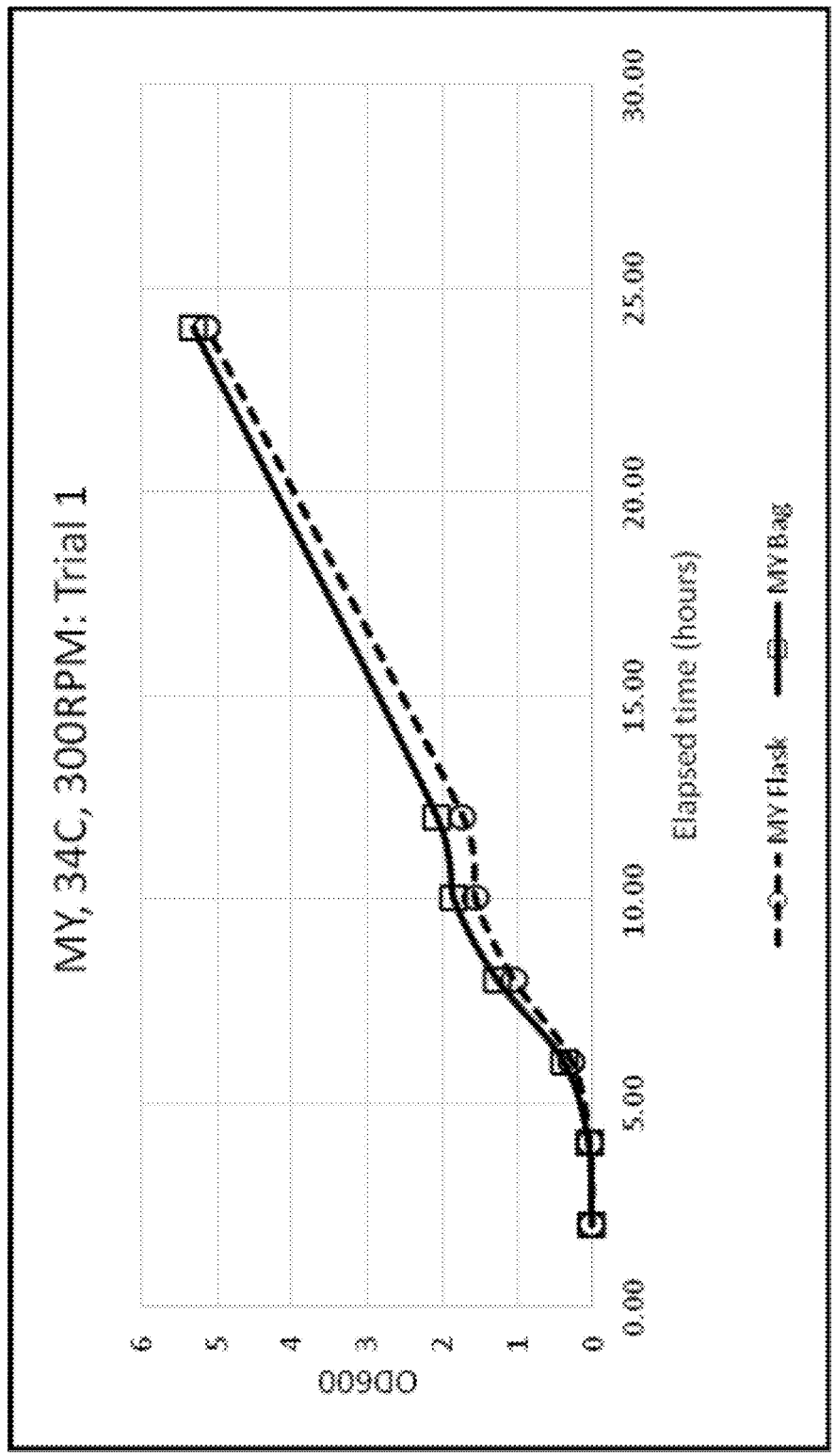
FIG. 9A is a graph illustrating the growth of bacteria in a LDPE bag according to the disclosed method compared to the growth of bacteria in a flask in a first trial using MY media (Maximum Yield media, Aldevron, Fargo, N. Dak.).
Figure 9B:
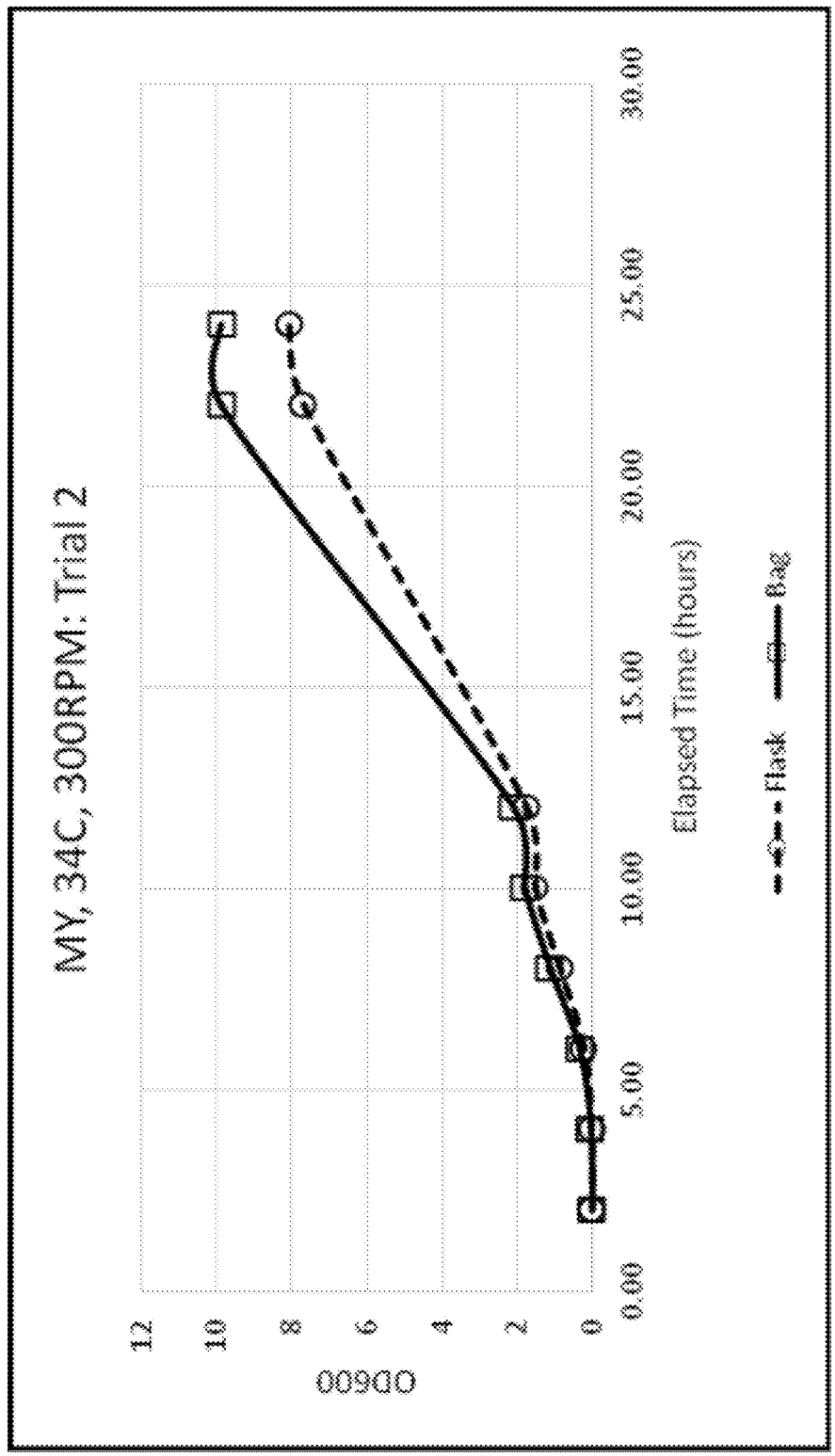
FIG. 9B is a graph illustrating the growth of bacteria in a LDPE bag according to the disclosed method compared to the growth of bacteria in a flask in a second trial using MY media.
Figure 9C:
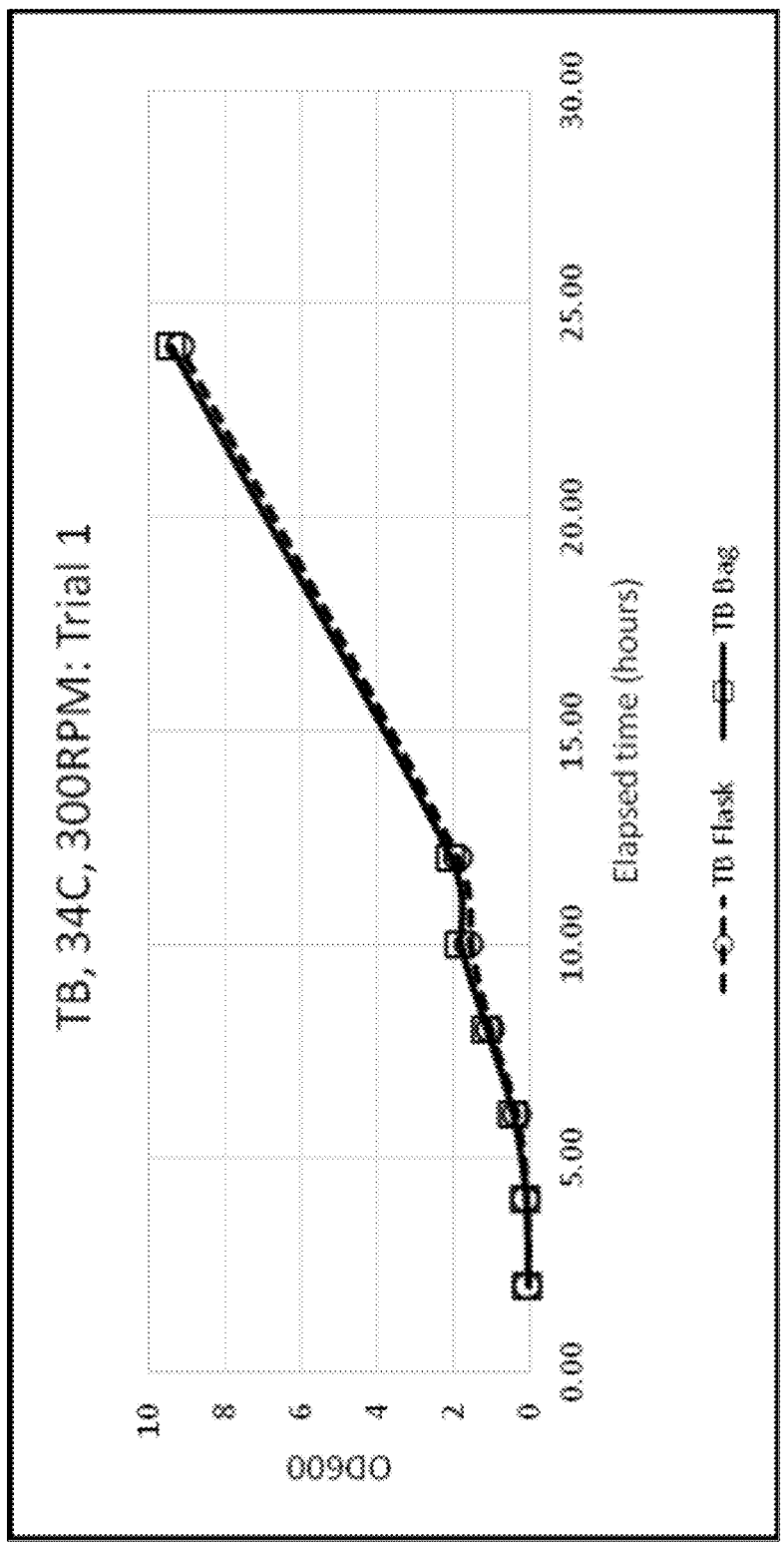
FIG. 9C is a graph illustrating the growth of bacteria in a LDPE bag according to the disclosed method compared to the growth of bacteria in a flask in a first trial using TB media.
Figure 9D:
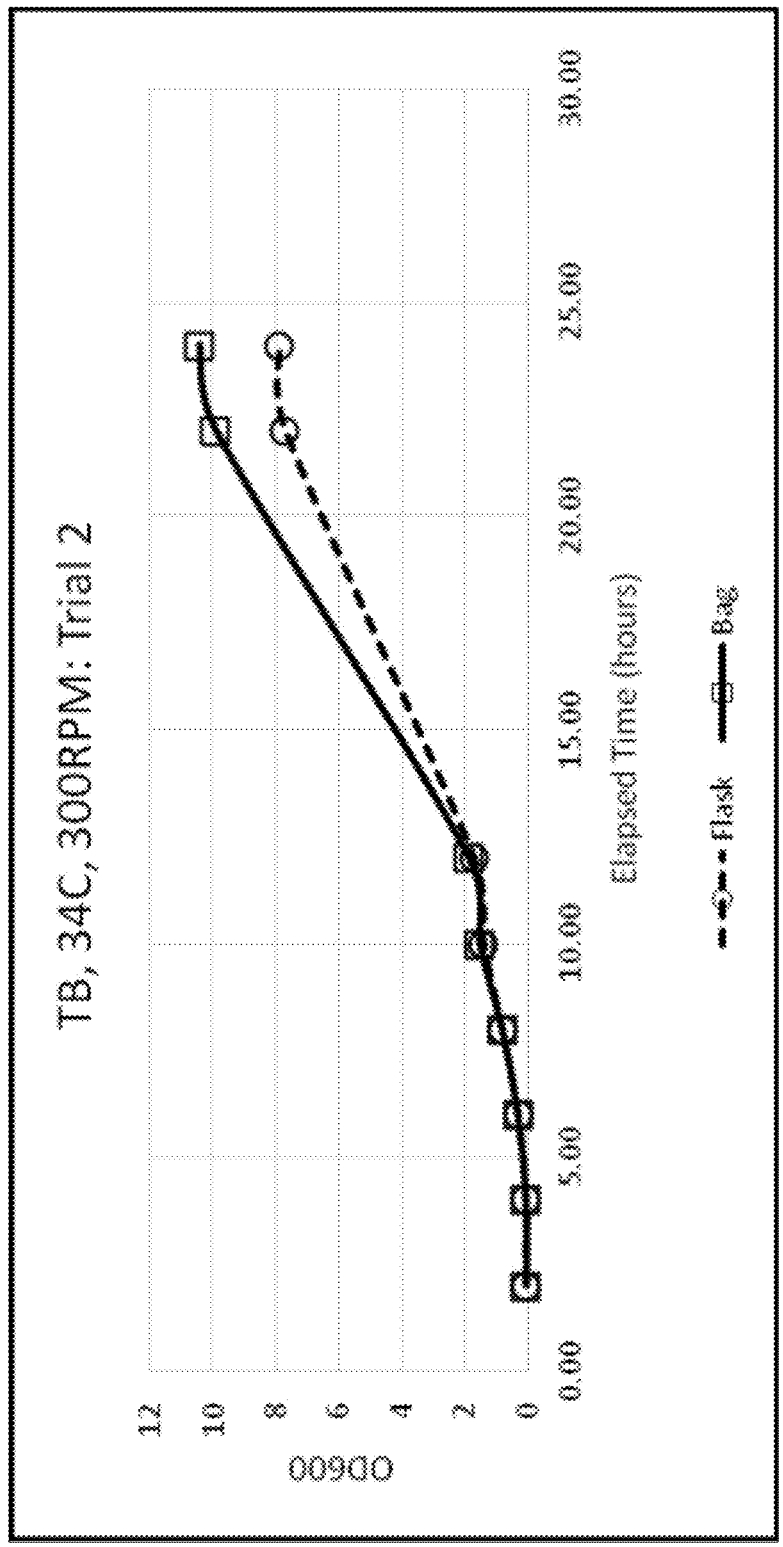
FIG. 9D is a graph illustrating the growth of bacteria in a LDPE bag according to the disclosed method compared to the growth of bacteria in a flask in a second trial using TB media.
Figure 9E:
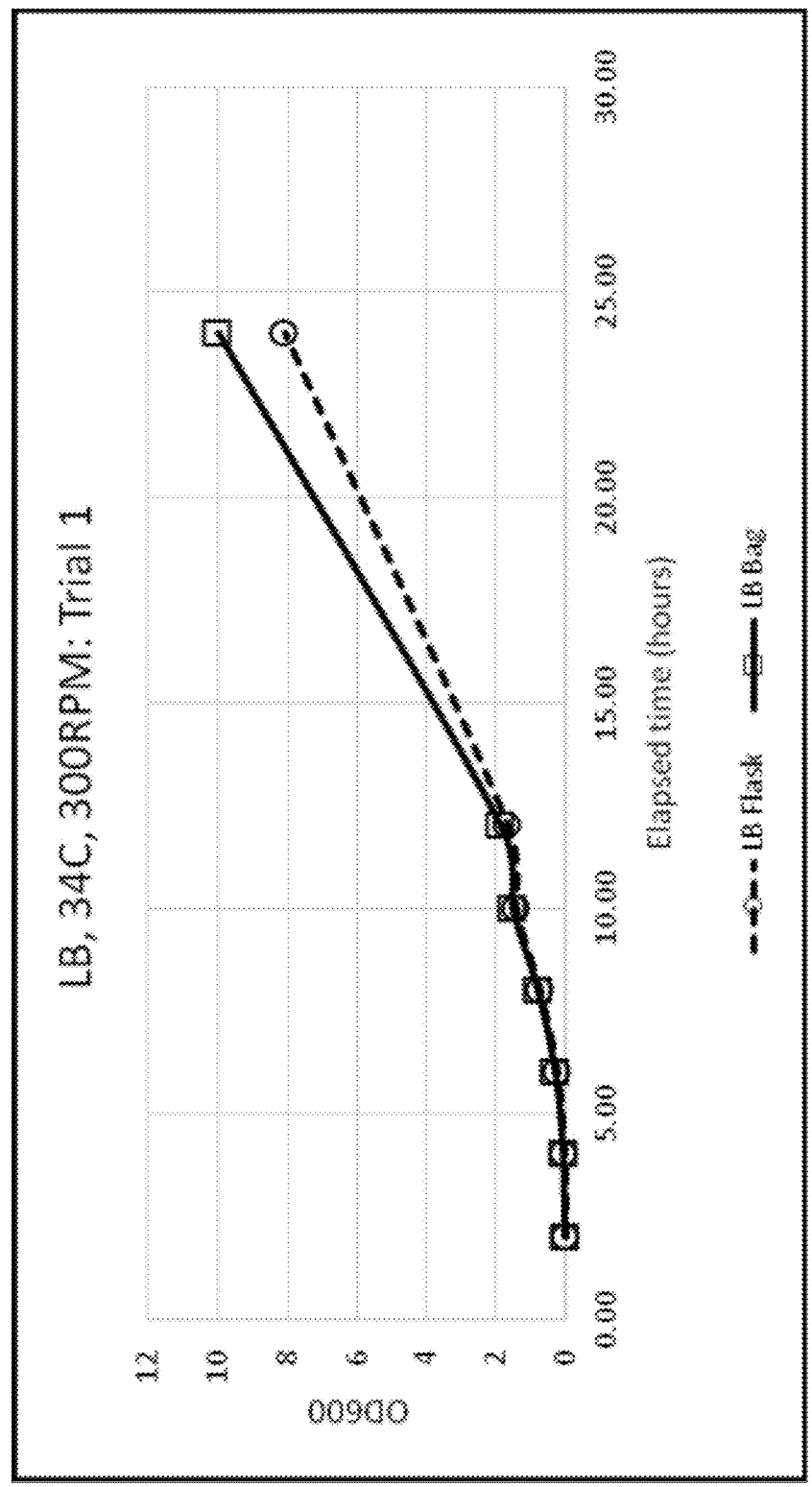
FIG. 9E is a graph illustrating the growth of bacteria in a LDPE bag according to the disclosed method compared to the growth of bacteria in a flask in a first trial using LB media.
Figure 9F:
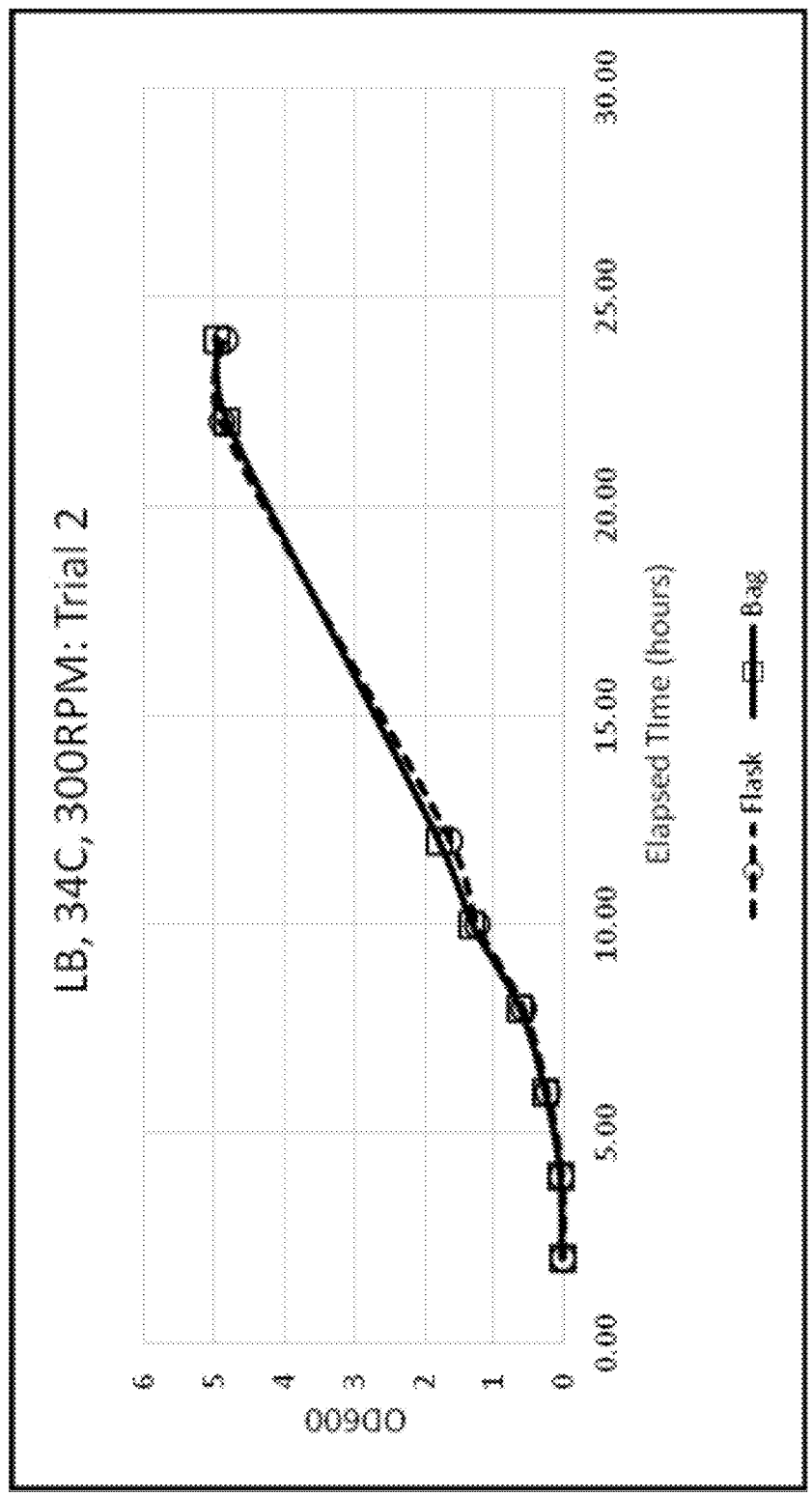
FIG. 9F is a graph illustrating the growth of bacteria in a LDPE bag according to the disclosed method compared to the growth of bacteria in a flask in a second trial using LB media.

FIGS. 9A-F record bacterial growth at 34° C., 300 rpm, using different media for growth in flasks and LDPE bags. FIG. 9A shows growth in a first trial using MY media, FIG. 9B shows growth in a second trial using MY media, FIG. 9C shows growth in a first trial using TB media. FIG. 9D shows growth in a second trial using TB media. FIG. 9E shows growth in a first trial using LB media. FIG. 9F shows growth in a second trial using LB media. Growth in LDPE bags resulted in equal or faster bacterial growth than that in conventional flasks. MY and TB media generally resulted in more bacterial host cell growth and higher plasmid yields than growth in LB media.

Figure 10:
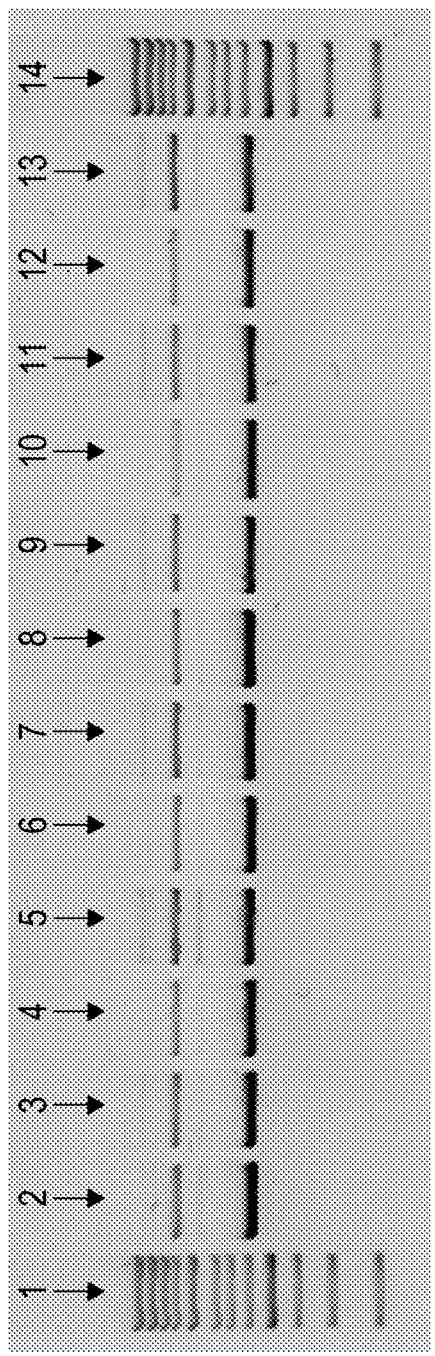
FIG. 10 is an image depicting plasmid DNA generated using the disclosed method of bacterial growth in LDPE bags, as well as plasmid DNA produced using flasks for bacterial growth using different types of media, and subjected to gel electrophoresis.

Cells were harvested by centrifugation at 10000×g and the weight of the cell pellet was measured. The cell pellet was resuspended and lysed to form a lysate and the plasmid was purified from the lysate using commercially available anion-exchange kits. Results are shown in FIG. 10, which is an image of a gel electrophoresis depicting plasmid DNA generated using the disclosed method of bacterial growth in LDPE bags, as well as plasmid DNA produced using flasks for bacterial growth at 34° C., an agitation rate of 300 rpm, and using different types of media. Lanes of the gel, from left to right, represent 1: a DNA ladder of molecular weight standards, 2: plasmid DNA from bacteria grown in a first flask using MY media, 3: plasmid DNA from bacteria grown in a second flask using MY media, 4: plasmid DNA from bacteria grown in a first LDPE bag using MY media, 5: plasmid DNA from bacteria grown in a second LDPE bag using MY media, 6: plasmid DNA from bacteria grown in a first flask using TB media, 7: plasmid DNA from bacteria grown in a second flask using TB media, 8: plasmid DNA from bacteria grown in a first LDPE bag using TB media, 9: plasmid DNA from bacteria grown in a second LDPE bag using TB media, 10: plasmid DNA from bacteria grown in a first flask using LB media, 11: plasmid DNA from bacteria grown in a second flask using LB media, 12: plasmid DNA from bacteria grown in a first LDPE bag using LB media, 13: plasmid DNA from bacteria grown in a second LDPE bag using LB media, and 14: a DNA ladder of molecular weight standards. MY and TB media generally resulted in more bacterial host cell growth and higher plasmid yields than growth in LB media, as evidenced by the generally larger and darker bands in MY and TB lanes relative to LB lanes.

Example 5

In this experiment, the growth of plasmid-containing bacterial cells in gas permeable LDPE bags is compared to their growth in 125 mL shake flasks. Identical conditions for flasks and LDPE bags are used for comparison. In each case, the plasmid with which the bacterial host cells are transformed is varied, and the growth conditions were adjusted based on the plasmid and host combination. In a first case with a pUMVC1-hpAP expression plasmid used in transformation, the conditions include: a growth temperature of 37° C., an agitation rate of 250 rpm, RG growth media, kanamycin selection, an Endura® *E. coli* strain (Lucigen, Middleton, Wis.), and a pUMVC1-hpAP plasmid (Aldevron, Fargo, N. Dak.) with a CMV IE promoter, trimmed intron A, rabbit beta-globin polyadenylation signal, and human placental alkaline phosphatase reporter gene. In a second case with a pALD-X80 expression plasmid used in transformation, the conditions include: a growth temperature of 34° C., an agitation rate of 250 rpm, RG growth media, kanamycin selection, an Endura® *E. coli* strain (Lucigen, Middleton, Wis.), and a pALD-X80 plasmid (Aldevron, Fargo, N. Dak.) with an AmpR promoter. In a third case with a pRc/CMV-HBs(S) expression plasmid used in transformation, the conditions include: a growth temperature of 34° C., an agitation rate of 250 rpm, RG growth media, ampicillin selection, an Endura® *E. coli* strain (Lucigen, Middleton, Wis.), and a pRc/CMV-HBs(S) plasmid (Aldevron, Fargo, N. Dak.) with a CMV IE promoter and expression of the hepatitis B surface antigen (HBsAg). The LDPE bags were medium size (about 8 inches by 10 inches).

Approximately 10 mL of LB soy media with kanamycin was added to a 50 mL tube. An isolated colony of host cells containing the pUMVC1-hpAP, pALD-X80, or pRc/CMV-HBs(S) plasmid from the plate were added to this tube using an inoculation loop. The tube was incubated at a 37° C. with 250 rpm agitation for 5-7 hours until the culture was turbid. A 125 mL shake flask and medium LDPE bag were each filled with 50 mL of the RG media with kanamycin or ampicillin, as described above. A 100 µL aliquot of the starter culture was used to inoculate the shake flask and the LDPE bag. The flask and LDPE bag were incubated at the growth temperature indicted above with an agitation rate of 250 rpm for 18 hours. Interim samples were collected at different time points to measure $OD_{600}$ and pH. The surface temperature of the flask and LDPE bag were measured using an IR gun thermometer when the interim samples were collected.

Figure 11A:
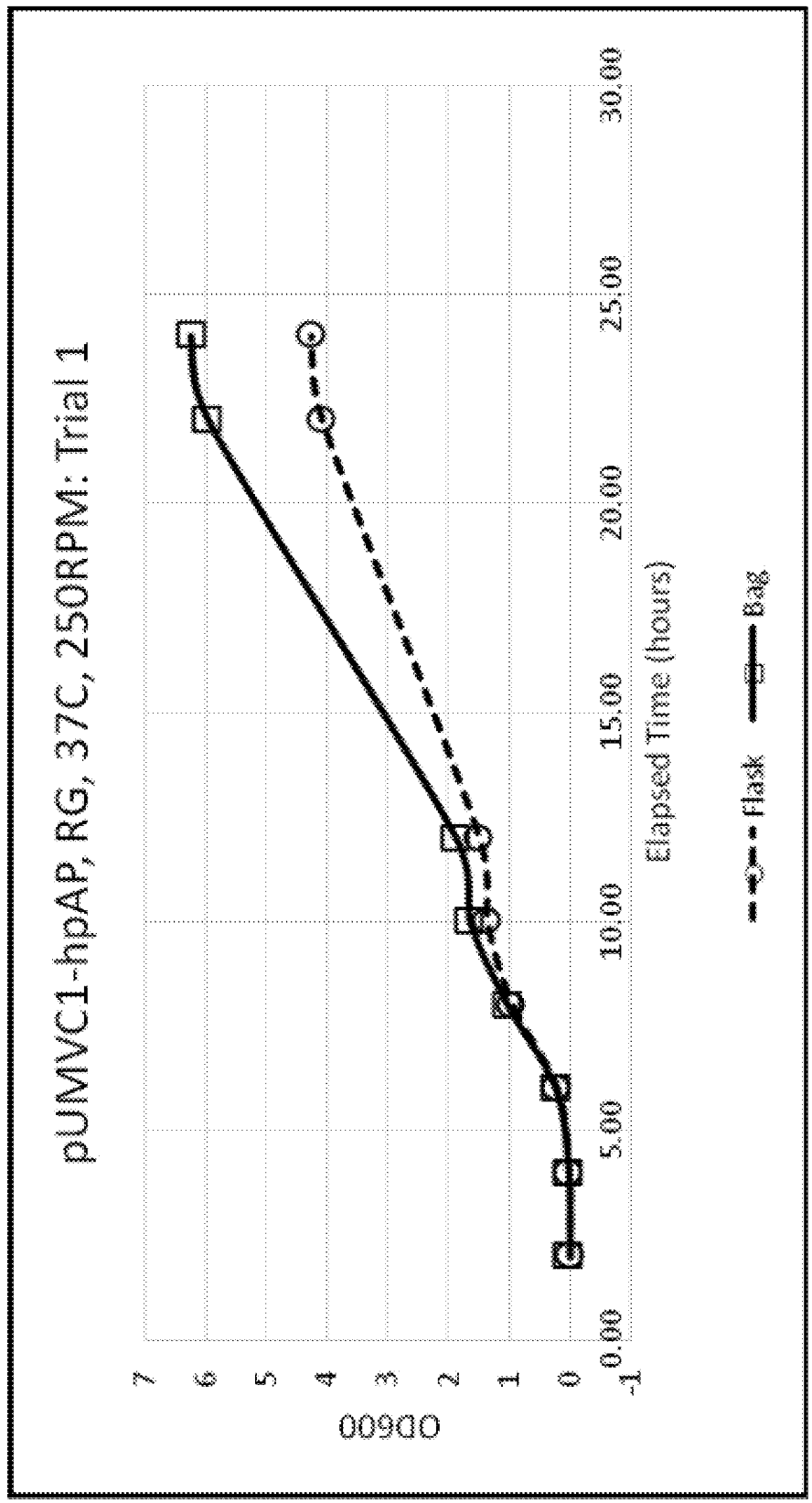
FIG. 11A is a graph illustrating the growth of bacteria in a LDPE bag according to the disclosed method compared to the growth of bacteria in a flask in a first trial with a pUMVC1-hpAP plasmid.
Figure 11B:
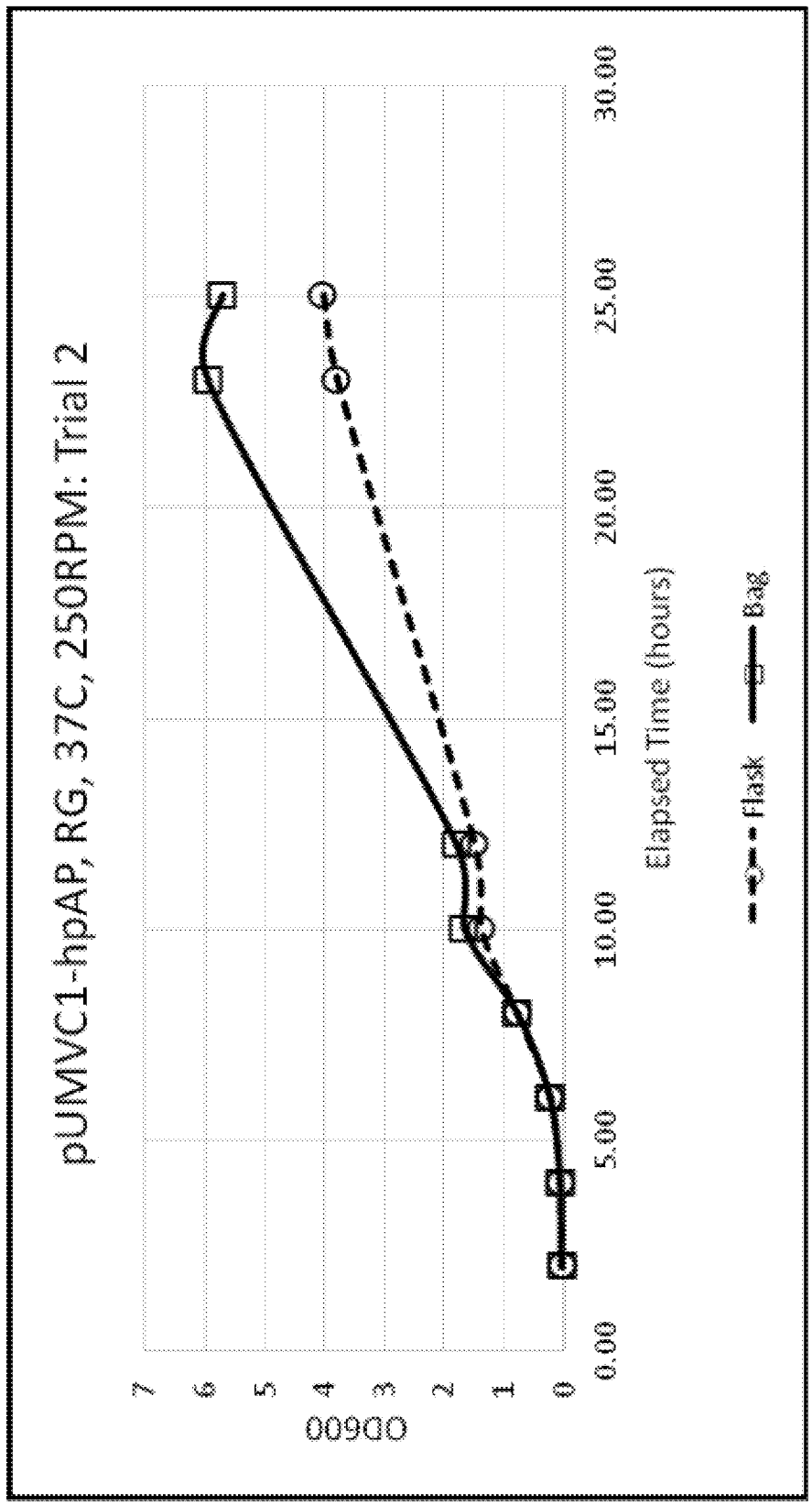
FIG. 11B is a graph illustrating the growth of bacteria in a LDPE bag according to the disclosed method compared to the growth of bacteria in a flask in a second trial with a pUMVC1-hpAP plasmid.
Figure 11C:
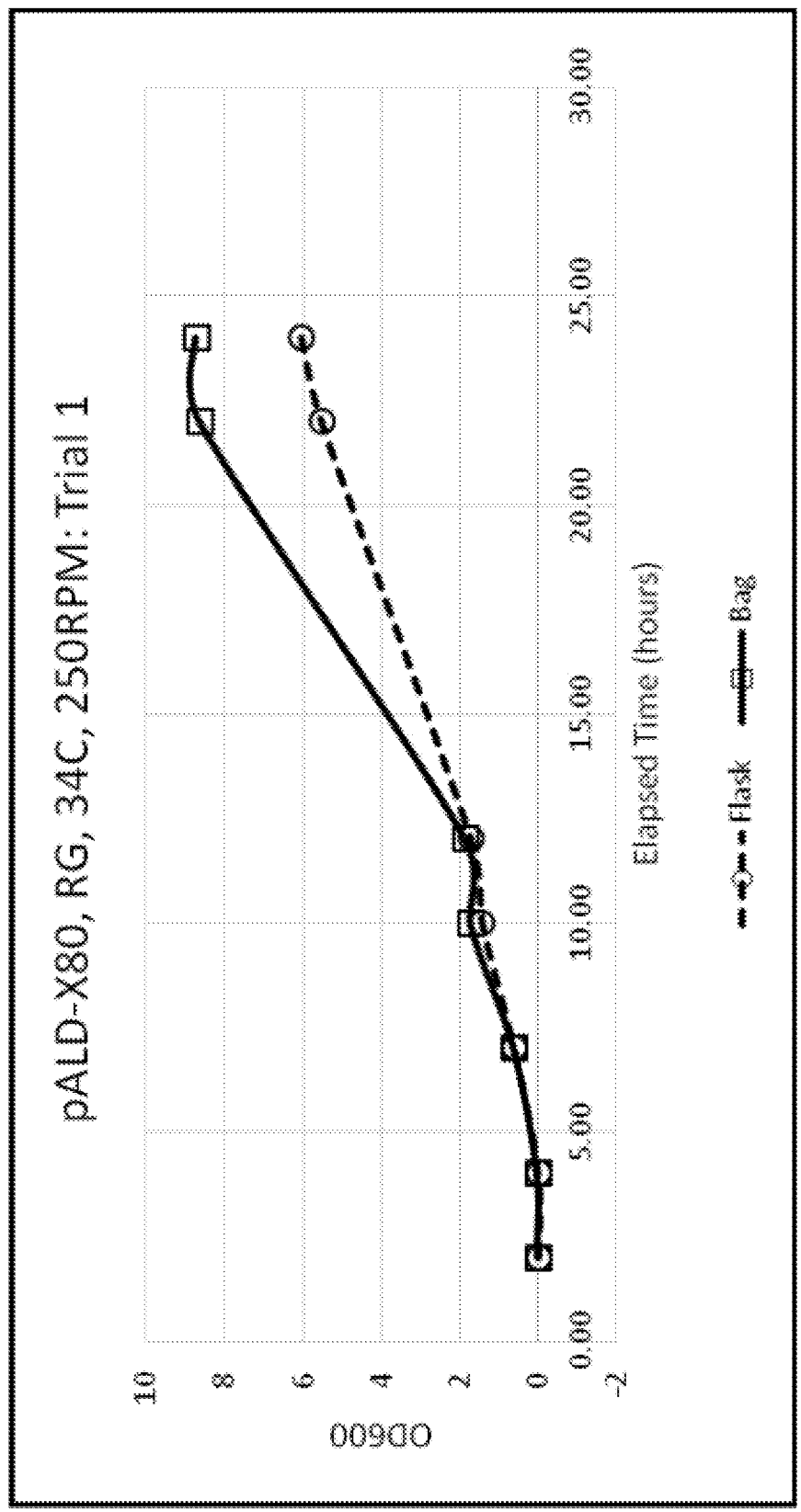
FIG. 11C is a graph illustrating the growth of bacteria in a LDPE bag according to the disclosed method compared to the growth of bacteria in a flask in a first trial with a pALD-X80 plasmid.
Figure 11D:
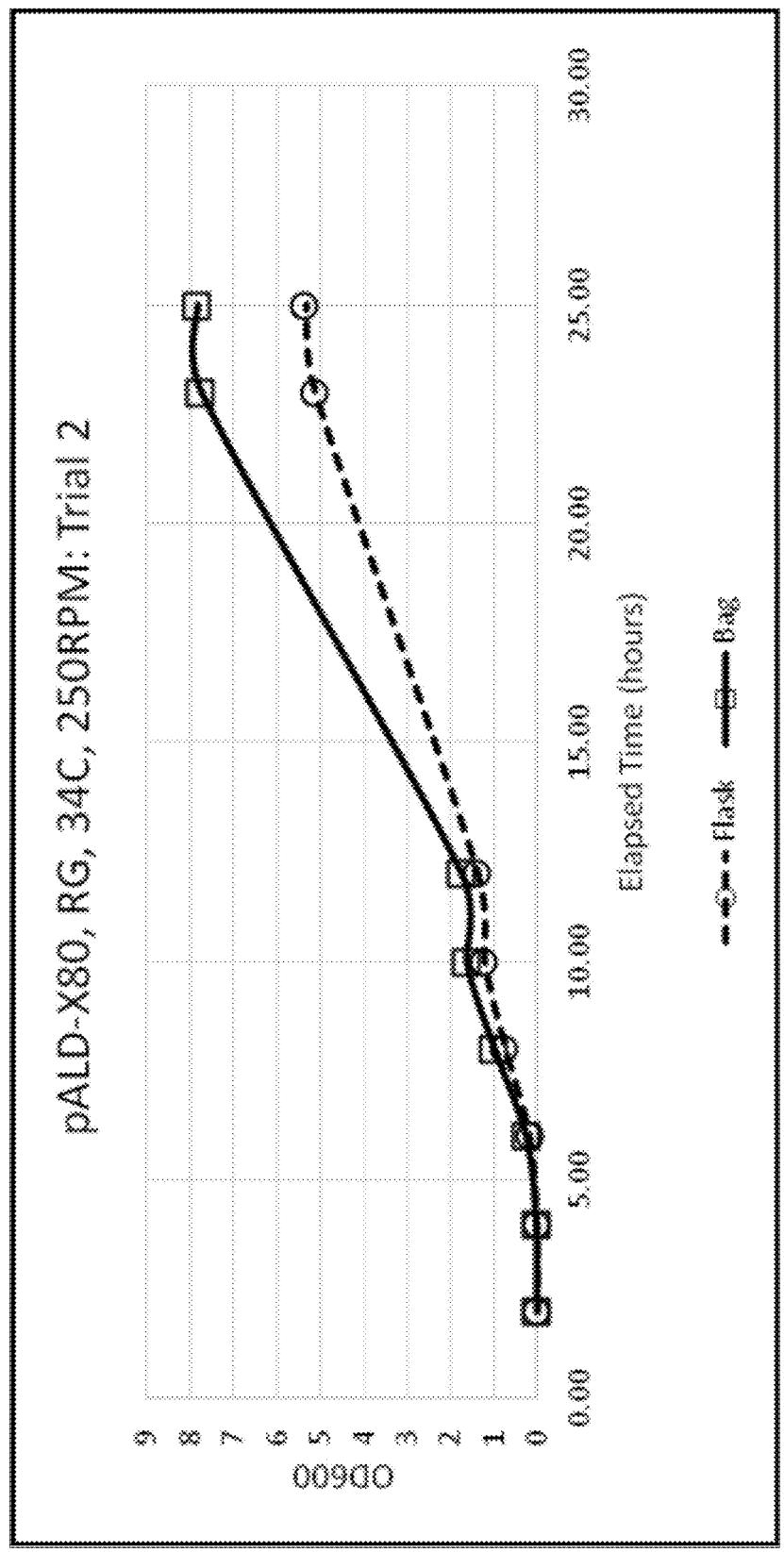
FIG. 11D is a graph illustrating the growth of bacteria in a LDPE bag according to the disclosed method compared to the growth of bacteria in a flask in a second trial with a pALD-X80 plasmid.
Figure 11E:
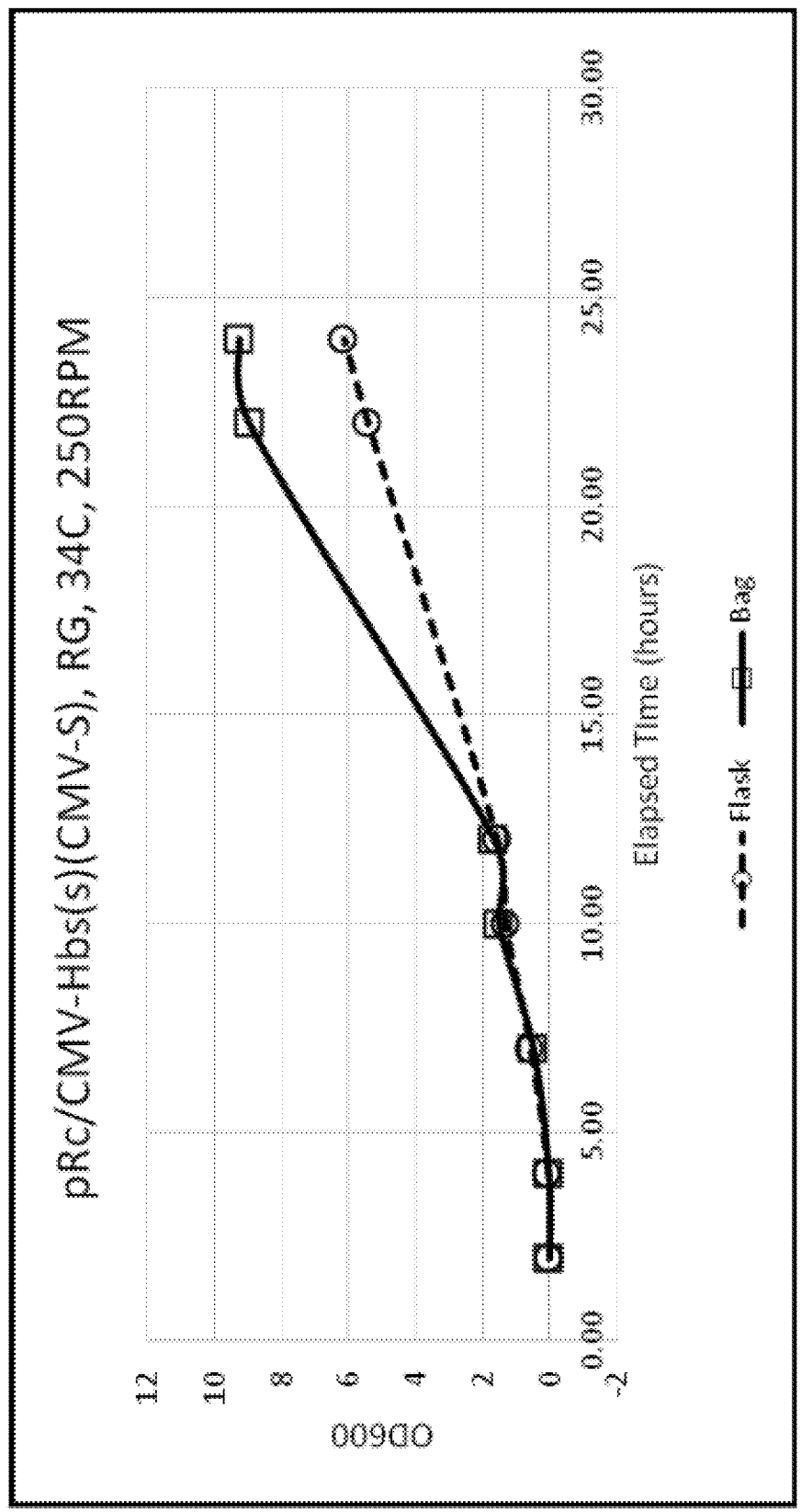
FIG. 11E is a graph illustrating the growth of bacteria in a LDPE bag according to the disclosed method compared to the growth of bacteria in a flask in a first trial with a pRc/CMV-HBs(S) plasmid.
Figure 11F:
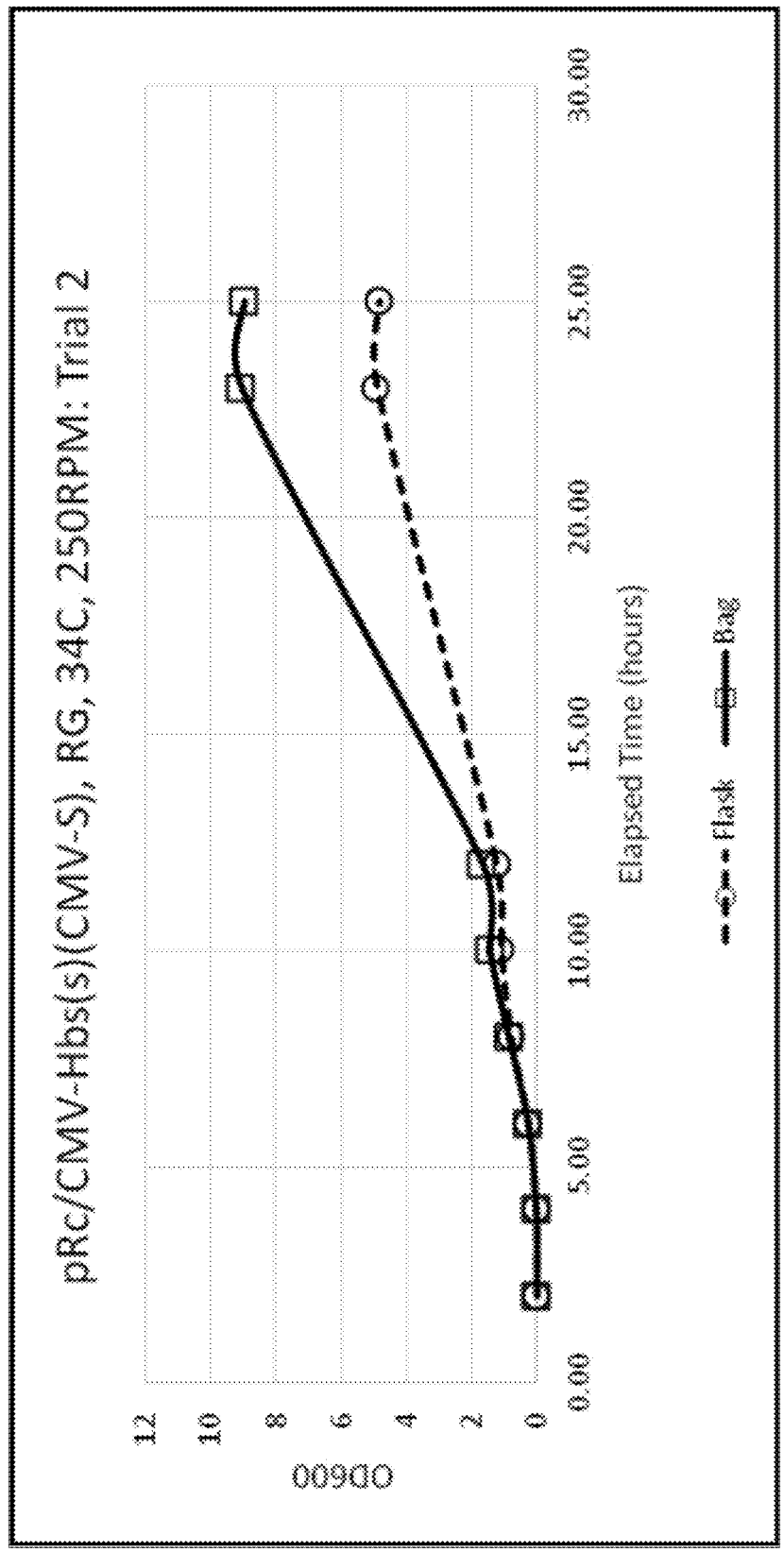
FIG. 11F is a graph illustrating the growth of bacteria in a LDPE bag according to the disclosed method compared to the growth of bacteria in a flask in a second trial with a pRc/CMV-HBs(S) plasmid.
Figure 12:
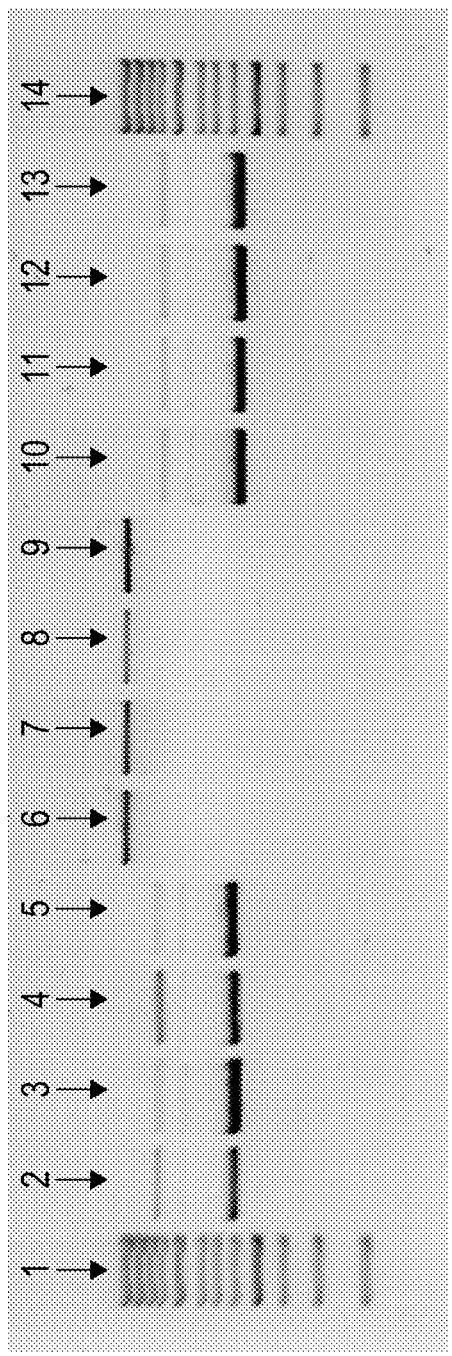
FIG. 12 is an image depicting plasmid DNA generated using the disclosed method of bacterial growth in LDPE bags, as well as plasmid DNA produced using flasks for bacterial growth with different plasmids, and subjected to gel electrophoresis.

FIGS. 11A-F record bacterial growth at 250 rpm in RG media, and using different plasmid expression vectors in flasks and LDPE bags is displayed. FIG. 11A shows growth in a first trial with a pUMVC1-hpAP plasmid at 37° C., FIG. 11B shows growth in a second trial with a pUMVC1-hpAP plasmid at 37° C., FIG. 11C shows growth in a first trial with a pALD-X80 plasmid at 34° C., FIG. 11D shows growth in a second trial with a pALD-X80 plasmid at 34° C., FIG. 11E shows growth in a first trial with a pRc/CMV-HBs(S) plasmid at 34° C., and FIG. 11F shows growth in a second trial with a pRc/CMV-HBs(S) plasmid at 34° C. Growth in LDPE bags resulted in generally faster bacterial growth than that in conventional flasks.

Cells were harvested by centrifugation at 10000×g and the weight of the cell pellet was measured. The cell pellet was resuspended and lysed to form a lysate and the plasmid was purified from the lysate using commercially available anion-exchange kits. Purified plasmid DNA is separated by gel electrophoresis in FIG. 12, which depicts plasmid DNA generated using the disclosed method of bacterial growth in LDPE bags, as well as plasmid DNA produced using flasks for bacterial growth with different plasmids. Lanes of the imaged gel, from left to right, represent 1: a DNA ladder of molecular weight standards, 2: plasmid DNA from bacteria grown in a first flask with a pUMVC1-hpAP plasmid, 3: plasmid DNA from bacteria grown in a second flask with a pUMVC1-hpAP plasmid, 4: plasmid DNA from bacteria grown in a first LDPE bag with a pUMVC1-hpAP plasmid, 5: plasmid DNA from bacteria grown in a second LDPE bag with a pUMVC1-hpAP plasmid, 6: plasmid DNA from bacteria grown in a first flask with a pALD-X80 plasmid, 7: plasmid DNA from bacteria grown in a second flask with a pALD-X80 plasmid, 8: plasmid DNA from bacteria grown in a first LDPE bag with a pALD-X80 plasmid, 9: plasmid DNA from bacteria grown in a second LDPE bag with a pALD-X80 plasmid, 10: plasmid DNA from bacteria grown in a first flask with a pRc/CMV-HBs(S) plasmid, 11: plasmid DNA from bacteria grown in a second flask with a pRc/CMV-HBs(S) plasmid, 12: plasmid DNA from bacteria grown in a first LDPE bag with a pRc/CMV-HBs(S) plasmid, 13: plasmid DNA from bacteria grown in a second LDPE bag with a pRc/CMV-HBs(S) plasmid, and 14: a DNA ladder of molecular weight standards. The differences in plasmid DNA molecular weights for each plasmid is evident from the location of the bands, and LDPE bags produced at least equal amounts of plasmid DNA relative to the plasmid DNA produced in conventional flasks.

Example 6

In this experiment, the growth in gas permeable LDPE bags of bacterial cells containing plasmids that contain genes for expression of different proteins is compared to growth in 125 mL shake flasks. Identical conditions for growth in flasks and LDPE bags are used for comparison. The protein-expressing plasmid with which the bacterial host cells is transformed was varied, and the growth conditions were adjusted based on the plasmid and host combination.

A BL21 *E. coli* strain (for example, New England Biolabs, Ipswich, Mass.) host was used for plasmids expressing 8× His NLS Cas9 protein grown at 37° C. and selected from a plate. The starter culture was incubated overnight at a temperature of 30° C., an agitation rate of 250 rpm, in 10 mL of LB growth media with kanamycin selection. The growth conditions in both 125 mL flasks and LDPE bags include: a growth temperature of 37° C., an agitation rate of 225 rpm, 50 mL of LB growth media, kanamycin selection, and 0.5 mL of the starter culture. The $OD_{600}$ reached before induction of protein expression was about 1.5 to 2, upon which the temperature was dropped to 25° C. and a 0.2% rhamnose inducing agent was added, followed by agitation at 225 rpm at 25° C. for about 18-20 hours.

A BL21 *E. coli* strain (for example, New England Biolabs, Ipswich, Mass.) host was used for plasmids expressing T7 RNA polymerase grown at 37° C. and selected from a plate. The starter culture was incubated overnight at a temperature of 30° C., an agitation rate of 250 rpm, in 10 mL of LB growth media with kanamycin selection. The growth conditions in both 125 mL flasks and LDPE bags include: a growth temperature of 37° C., an agitation rate of 225 rpm, 50 mL of TB growth media, kanamycin selection, and 0.5 mL of the starter culture. The $OD_{600}$ reached before induction of protein expression was about 0.4±0.1, upon which the temperature was dropped to 25° C. and a 1.0% rhamnose inducing agent was added, followed by agitation at 225 rpm at 25° C. for about 18-20 hours.

Figure 13:
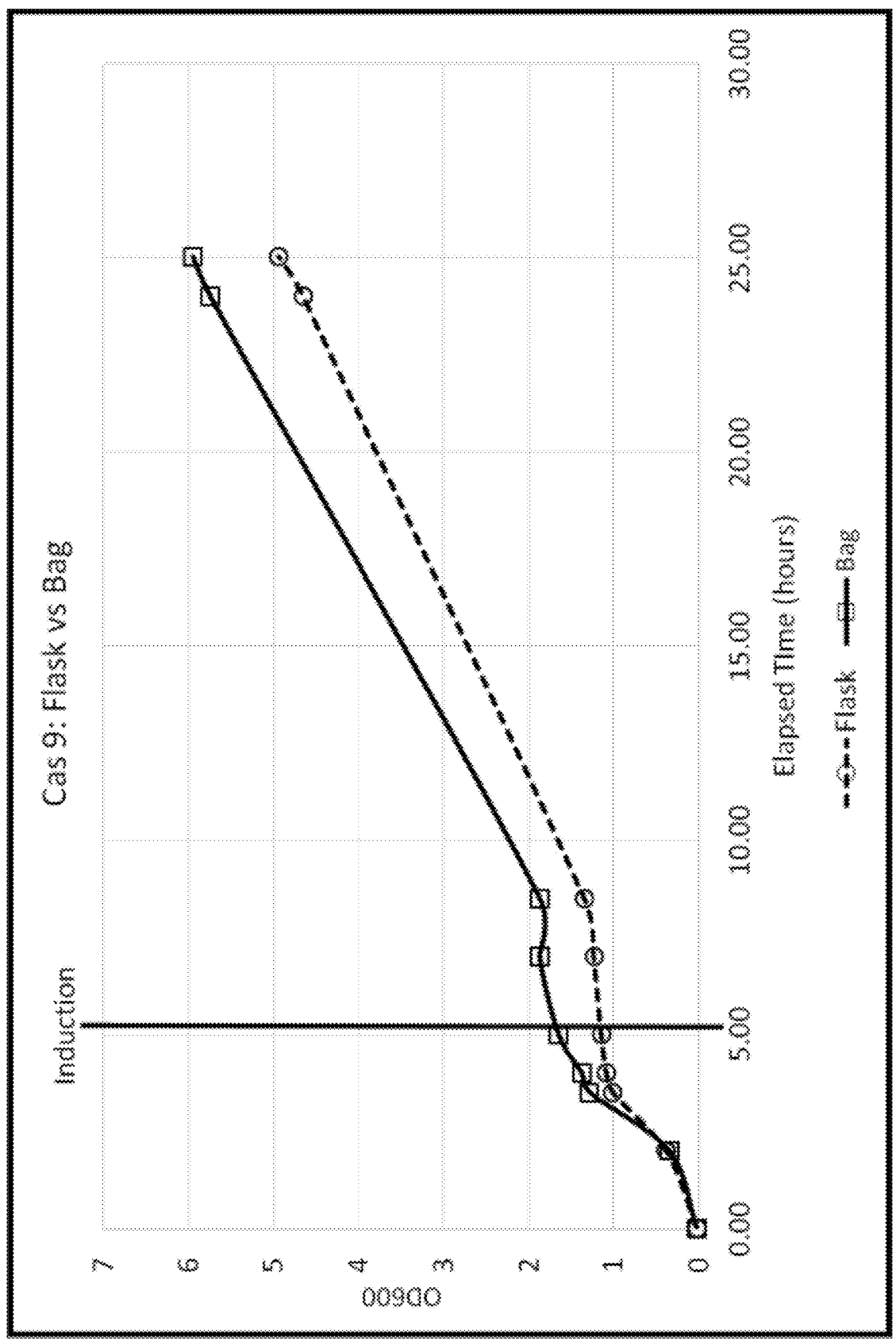
FIG. 13 is a graph illustrating the growth of bacteria in a LDPE bag according to the disclosed method compared to the growth of bacteria in a flask for the expression of Cas9. Induction of protein expression begins at approximately 5 hours of elapsed time.
Figure 15:
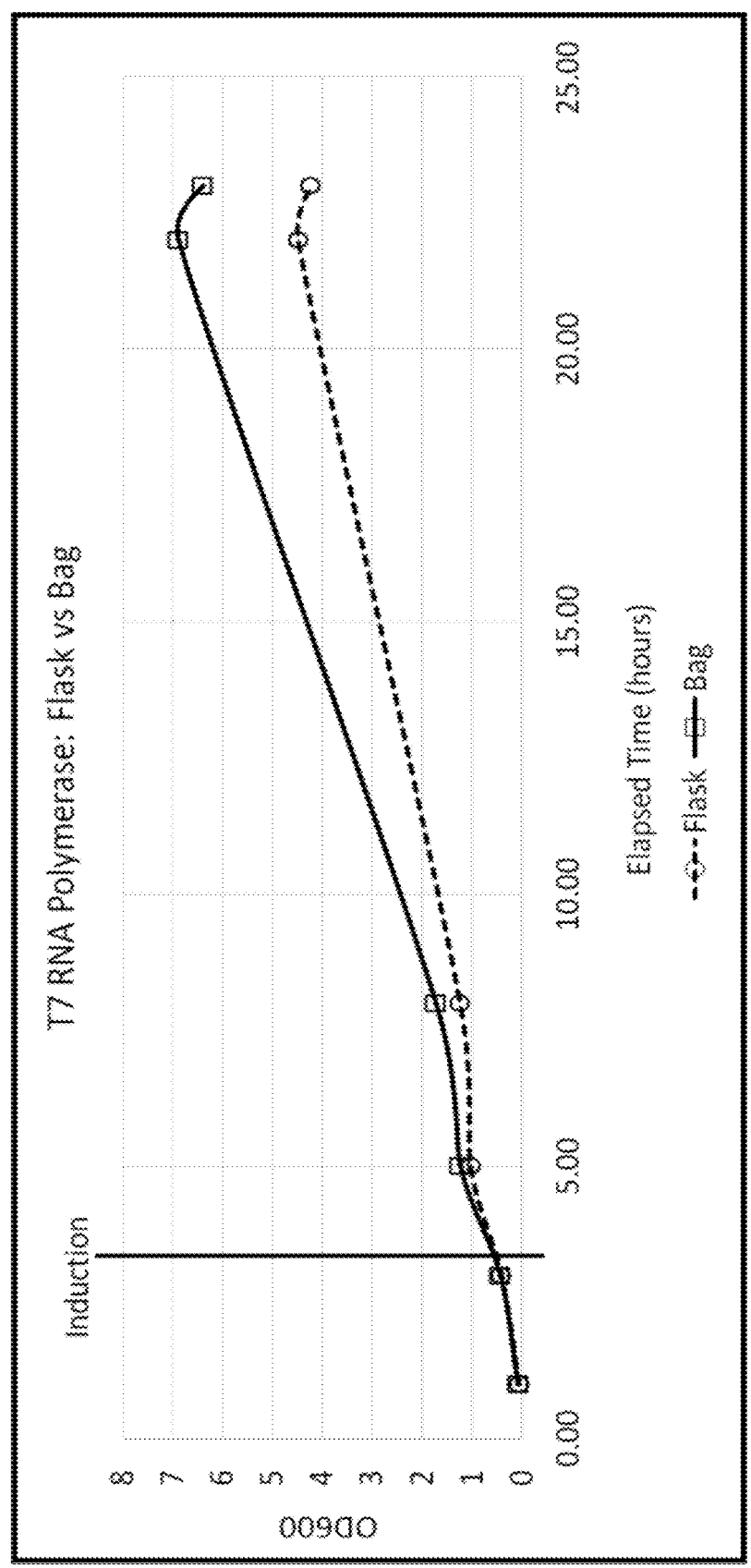
FIG. 15 is a graph illustrating the growth of bacteria in a LDPE bag according to the disclosed method compared to the growth of bacteria in a flask for the expression of T7 RNA polymerase. Induction of protein expression begins between approximately 3 and 4 hours of elapsed time.

Interim samples were collected at different time points to measure $OD_{600}$, pH, and protein expression. The surface temperature of the flask or LDPE bag were measured using an IR gun thermometer. In FIGS. 13 and 15, bacterial growth over time for host cells capable of expressing the varying proteins was compared for growth in flasks and LDPE bags. In FIG. 13, growth conditions were as described above for the 8× His NLS Cas9 protein expression system. In FIG. 15, growth conditions were as described above for the T7 RNA polymerase expression system. In each case, bacterial growth in LDPE bags was greater than or equal to bacterial growth in flasks by the point of protein expression induction. After induction, bacterial growth continued to increase in both flasks and LDPE bags, with bacterial growth in LDPE bags generally exceeding bacterial growth in flasks.

Figure 14:
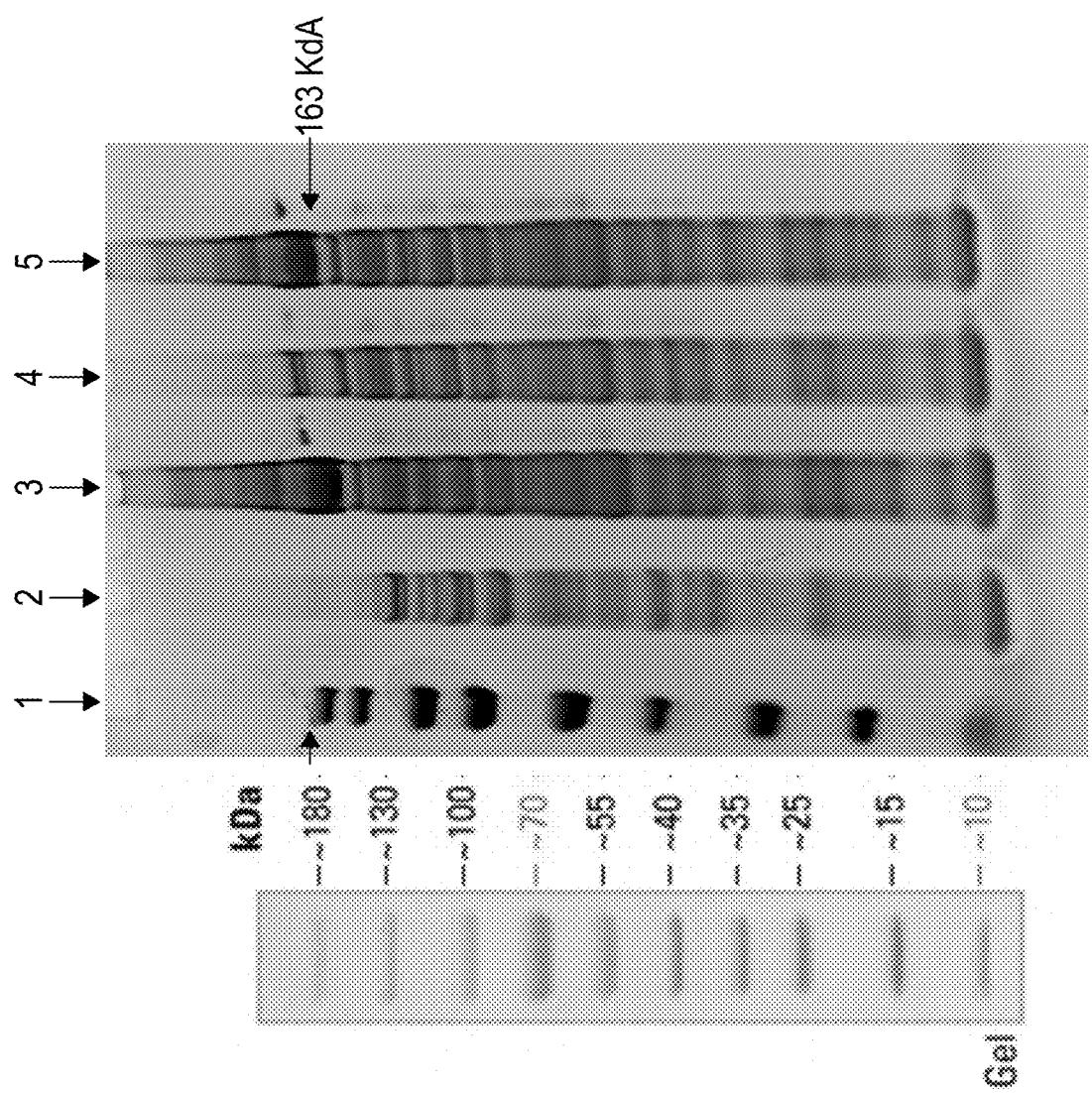
FIG. 14 is an image of an SDS-PAGE (SDS-polyacrylamide gel electrophoresis) depicting Cas9 protein expressed in bacteria grown using the disclosed method of bacterial growth in LDPE bags, as well as Cas9 protein expressed in bacteria grown using flasks for bacterial growth.
Figure 16:
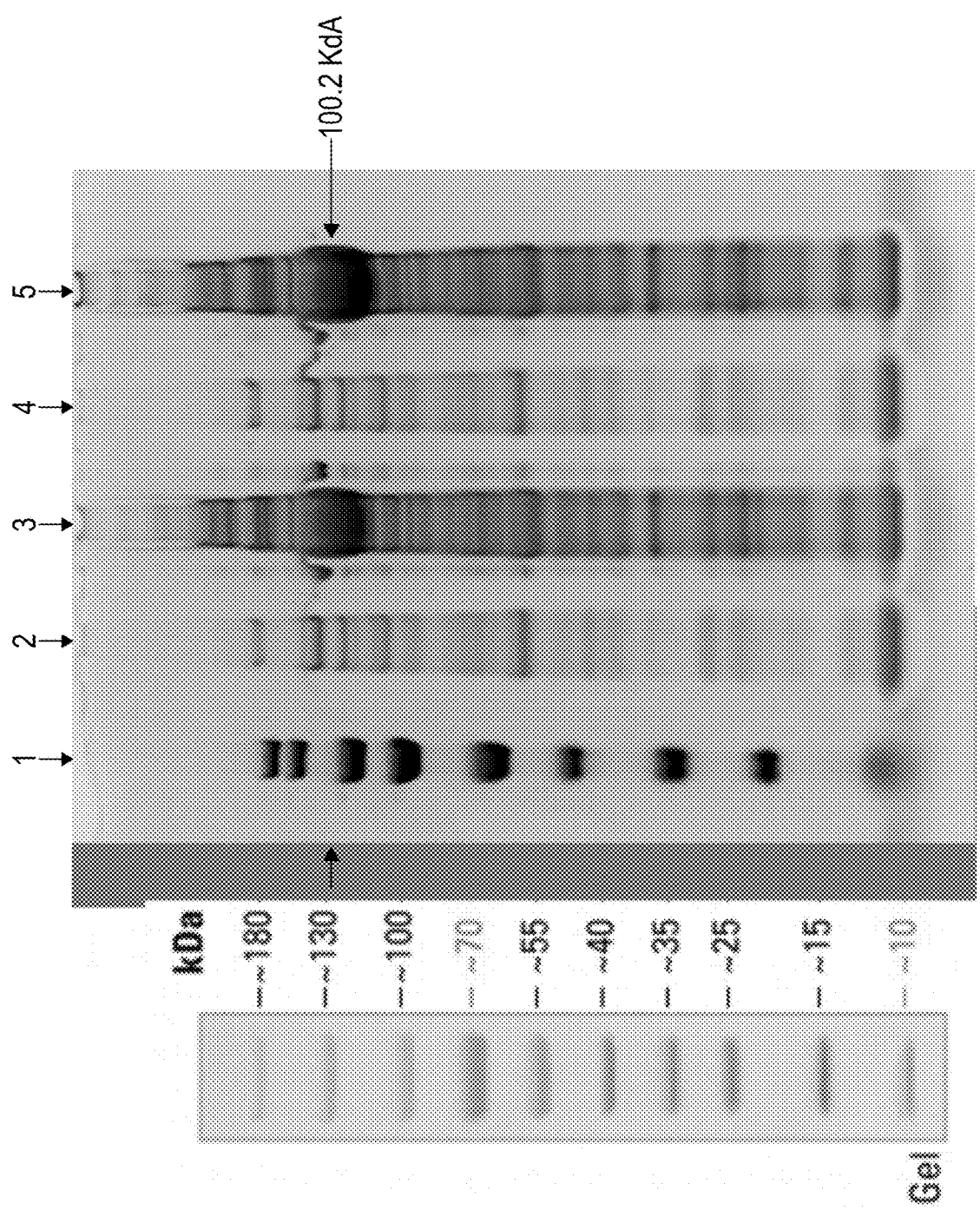
FIG. 16 is an image of an SDS-PAGE depicting T7 RNA polymerase expressed in bacteria grown using the disclosed method of bacterial growth in LDPE bags, as well as T7 RNA polymerase expressed in bacteria grown using flasks for bacterial growth.

After induction was complete, cells were harvested by centrifugation at 10000×g and the weight of the cell pellet was measured. The cell pellet was lysed to form a lysate and the expressed protein was purified from the lysate using commercial means, such as affinity chromatography systems. For example, Cas9 protein is purified by affinity chromatography using a nickel affinity column, followed by hydrophobic interaction chromatography. In another example, T7 polymerase is purified by affinity chromatography using a nickel affinity column, followed by charge-based purification chromatography. Protein purity is characterized using SDS-PAGE, as shown in FIGS. 14 and 16. In FIG. 14, Cas9 expression is evaluated, where Cas9 is indicated by a band at approximately 163 kDa. The left inset image represents a protein ladder for about 10 to about 180 kDa. Lanes of the imaged gel, from left to right, represent 1: the protein ladder, 2: protein expressed in bacteria grown in a flask before the induction of protein expression, 3: protein expressed in bacteria grown in a flask after the induction of protein expression, 4: protein expressed in bacteria grown in a LDPE bag before the induction of protein expression, and 5: protein expressed in bacteria grown in a LDPE bag after the induction of protein expression. Protein expression after induction was greater than that before induction for both flask and LDPE bag bacteria growth conditions. Additionally, protein purity was equal or greater from LDPE bag growth conditions relative to flask growth conditions.

In FIG. 16, T7 RNA polymerase expression is evaluated, where T7 RNA polymerase is indicated by a band at approximately 100.2 kDa. The left inset image represents a protein ladder for about 10 to about 180 kDa. Lanes of the imaged gel, from left to right, represent 1: the protein ladder, 2: protein expressed in bacteria grown in a flask before the induction of protein expression, 3: protein expressed in bacteria grown in a flask after the induction of protein expression, 4: protein expressed in bacteria grown in a LDPE bag before the induction of protein expression, and 5: protein expressed in bacteria grown in a LDPE bag after the induction of protein expression. Protein expression after induction was greater than that before induction for both flask and LDPE bag bacteria growth conditions. Additionally, protein purity was equal or greater from LDPE bag growth conditions relative to flask growth conditions.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

I claim:

1. A method of growing bacterial host cells in a gas-permeable bag comprising the steps of:
providing a starter culture of bacterial host cells, wherein the starter culture comprises at least one colony of the host cells transformed with plasmids comprising an antibiotic resistance gene;
providing the gas-permeable bag;
adding media, an antibiotic, and the starter culture host cells to the gas-permeable bag to form a main culture, wherein the antibiotic is selected such that starter culture host cells expressing the antibiotic resistance gene are viable in the presence of the antibiotic; and
incubating the gas-permeable bag containing the main culture such that host cells grow to a desired concentration.

2. The method of claim 1, wherein the host cells are *E. coli* cells.

3. The method of claim 1, wherein the gas-permeable bag is a low-density polyethylene (LDPE) bag.

4. The method of claim 3, wherein an opening of the LDPE bag is sealable, such that the LDPE bag is closed to an external environment when sealed.

5. The method of claim 4, wherein the LDPE bag comprises multiple panels configured to be pressed together to form a liquid-tight seal.

6. The method of claim 1, wherein the plasmids further comprise a DNA sequence encoding a protein to be expressed.

7. The method of claim 1, wherein 50 mL to 1 L of media is added to the gas-permeable bag.

8. The method of claim 1, wherein the step of incubating of the gas-permeable bag containing the main culture further comprises agitation at 200 to 500 rpm at a temperature of 30° C. to 42° C.

9. The method of claim 1, wherein the desired concentration is indicated by an $OD_{600}$ of 0.1 to 2.

10. A method of producing plasmid DNA from bacterial host cells grown in a gas-permeable low-density polyethylene (LDPE) bag comprising the steps of:
providing the LDPE bag;
adding media, an antibiotic, and host cells to the LDPE bag to form a main culture, wherein at least a portion of the host cells are transformed with plasmids comprising a DNA sequence encoding a protein and an antibiotic resistance gene, and wherein the antibiotic is selected such that host cells expressing the antibiotic resistance gene are viable in the presence of the antibiotic;
incubating the LDPE bag containing the main culture;
measuring an $OD_{600}$ of the main culture;
harvesting host cells from the main culture when a host cell concentration, indicated by the $OD_{600}$, reaches a desired concentration;
pelleting the host cells using centrifugation to form a pellet of the host cells; and
resuspending and lysing the pellet of the host cells to obtain a lysate comprising plasmid DNA produced by the host cells.

11. The method of claim 10, wherein the LDPE bag is sealable and comprises multiple panels wherein the panels are configured to be pressed together to form a liquid-tight seal, such that the LDPE bag is closed to an external environment when sealed.

12. The method of claim 10, wherein 50 mL to 1 L of media is added to the LDPE bag.

13. The method of claim 10, wherein the step of incubating of the LDPE bag containing the main culture further comprises agitation at 200 to 500 rpm at a temperature of 30° C. to 42° C.

14. The method of claim 10, wherein the desired concentration is indicated by an $OD_{600}$ of 0.1 to 2.

15. The method of claim 10, further comprising the step of separating cellular components of the host cells from the plasmid DNA in the lysate.

16. A method of expressing a protein in bacterial host cells grown in a gas-permeable low-density polyethylene (LDPE) bag comprising the steps of:
provided the LDPE bag;
adding 50 mL to 1 L of media, an antibiotic, and host cells to the LDPE bag to form a main culture, wherein at least a portion of the host cells are transformed with plasmids comprising a DNA sequence encoding the protein and an antibiotic resistance gene, and wherein the antibiotic is selected such that host cells expressing the antibiotic resistance gene are viable in the presence of the antibiotic;
incubating the LDPE bag containing the main culture at a growth temperature until the host cell concentration reaches a desired concentration indicated by an $OD_{600}$ of 0.1 to 2; and
inducing the expression of the protein by the host cells of the main culture.

17. The method of claim 16, wherein the step of incubating of the LDPE bag containing the main culture further comprises agitation at 200 to 500 rpm and wherein the growth temperature is 30° C. to 42° C.

18. The method of claim 16, wherein the induction comprises the addition of an inducing agent to the main culture.

19. The method of claim 16, wherein the induction comprises reducing the growth temperature to an induction temperature of 15° C. to 37° C.

20. The method of claim 16, further comprising the steps of harvesting host cells from the main culture, pelleting the host cells using centrifugation to form a pellet of host cells, resuspending and lysing the pellet of the host cells to form a lysate, and purifying the protein from the lysate.

* * * * *